US 6,413,273 B1

(12) United States Patent
Baum et al.

(10) Patent No.: US 6,413,273 B1
(45) Date of Patent: *Jul. 2, 2002

(54) METHOD AND SYSTEM FOR TEMPORARILY SUPPORTING A TUBULAR ORGAN

(75) Inventors: Abraham Baum, Givataim; Elisha Hoch, Rehovot; Israel Schnitzer, Tel Aviv; Lior Kacir, Rehovot; Felix Rabinovich, Rishon Lezion; Ilia Rueben, Beersheva, all of (IL)

(73) Assignee: Israel Aircraft Industries Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/329,839

(22) Filed: Jun. 10, 1999

Related U.S. Application Data

(63) Continuation-in-part of application No. 09/274,851, filed on Mar. 23, 1999, now Pat. No. 6,258,118, which is a continuation-in-part of application No. 09/199,556, filed on Nov. 25, 1998.

(51) Int. Cl.⁷ .................................................. A61F 2/06
(52) U.S. Cl. ....................................... 623/1.19; 606/198
(58) Field of Search ............................... 623/1.19, 1.18, 623/1.15, 1.22, 1.3; 606/191, 192, 198, 200, 108, 194, 78; 604/104, 105, 531, 532, 280, 281, 282

(56) References Cited

U.S. PATENT DOCUMENTS

| | | | |
|---|---|---|---|
| 4,411,655 A | 10/1983 | Schreck | 604/165 |
| 4,919,133 A | 4/1990 | Chiang | 606/159 |
| 4,991,602 A | 2/1991 | Amplatz et al. | 128/772 |
| 5,143,085 A | 9/1992 | Wilson | 128/772 |
| 5,147,370 A | 9/1992 | McNamara et al. | 606/108 |
| 5,197,978 A | 3/1993 | Hess | 623/1 |
| 5,211,183 A | 5/1993 | Wilson | 128/772 |
| 5,242,451 A | 9/1993 | Harada et al. | 606/108 |
| 5,354,308 A | 10/1994 | Simon et al. | 606/198 |
| 5,354,309 A | 10/1994 | Schnepp-Pesch et al. | 606/198 |
| 5,370,683 A | 12/1994 | Fontaine | 623/1 |
| 5,372,600 A | 12/1994 | Beyar et al. | 606/108 |
| 5,405,377 A | 4/1995 | Cragg | 623/1 |
| 5,433,723 A | 7/1995 | Lindenberg et al. | 606/198 |
| 5,441,516 A | 8/1995 | Wang | |
| 5,449,372 A | 9/1995 | Schmaltz | |
| 5,456,667 A | 10/1995 | Ham et al. | 604/107 |
| 5,465,717 A | 11/1995 | Imran et al. | 128/642 |
| 5,503,636 A | 4/1996 | Schmitt | |
| 5,523,092 A | 6/1996 | Hanson | |
| 5,540,712 A | 7/1996 | Kleshinski et al. | 606/198 |
| 5,540,713 A | 7/1996 | Schnepp-Pesch et al. | 606/198 |
| 5,545,210 A | 8/1996 | Hess et al. | 623/1 |
| 5,554,181 A | 9/1996 | Das | 623/1 |
| 5,562,641 A | 10/1996 | Flomenblit et al. | 604/281 |
| 5,573,509 A | 11/1996 | Thomton | 604/102 |
| 5,601,593 A | 2/1997 | Freitag | 606/198 |
| 5,617,854 A | 4/1997 | Munsif | 128/642 |
| 5,618,299 A | 4/1997 | Khosravi et al. | 606/198 |
| 5,624,508 A | 4/1997 | Flomenblit et al. | 148/510 |
| 5,667,522 A | 9/1997 | Flomenblit et al. | 606/198 |
| 5,674,241 A | 10/1997 | Bley et al. | 606/198 |
| 5,676,685 A | 10/1997 | Razavi | 606/194 |
| 5,690,671 A | 11/1997 | McGurk et al. | 606/200 |
| 5,716,410 A | * | 2/1998 | Wang et al. | 623/12 |
| 5,725,549 A | | 3/1998 | Lam | 606/198 |
| 5,741,249 A | | 4/1998 | Moss et al. | 606/33 |
| 5,976,152 A | * | 11/1999 | Regan et al. | 623/1 |

* cited by examiner

Primary Examiner—Michael H. Thaler
Assistant Examiner—Vy Q. Bui
(74) Attorney, Agent, or Firm—Paul J. Sutton

(57) ABSTRACT

System and method for opening and temporarily supporting a section of a generally tubular organ, the system includes a dilation catheter, the dilation catheter includes an integrally connected shape memory catheter tip, the shape memory catheter tip, is made of a shape memory alloy, wherein said shape memory catheter tip assumes a first shape at a first temperature and a second shape at a second temperature.

8 Claims, 30 Drawing Sheets

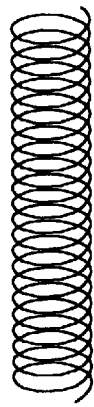
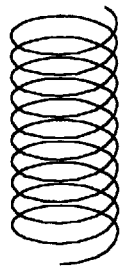
FIG. 1A
PRIOR ART
FIG. 1B
PRIOR ART
FIG. 1C
PRIOR ART
FIG. 1D
PRIOR ART
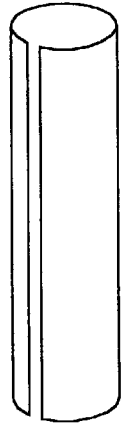
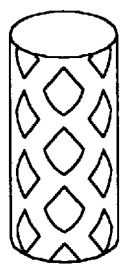
FIG. 1E
PRIOR ART
FIG. 1F
PRIOR ART
FIG. 1G
PRIOR ART
FIG. 1H
PRIOR ART

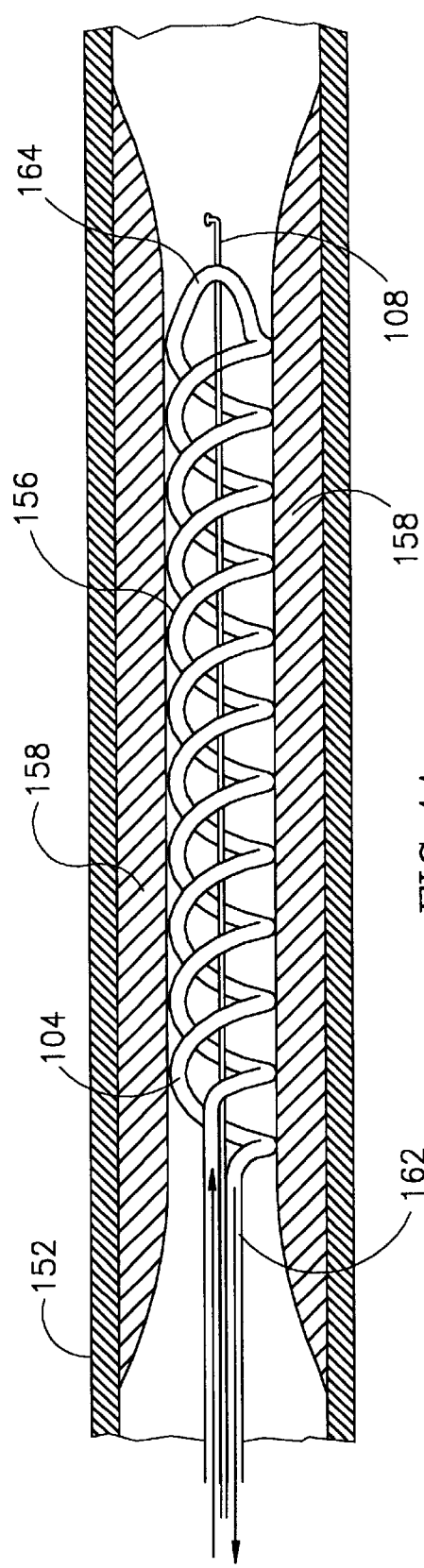
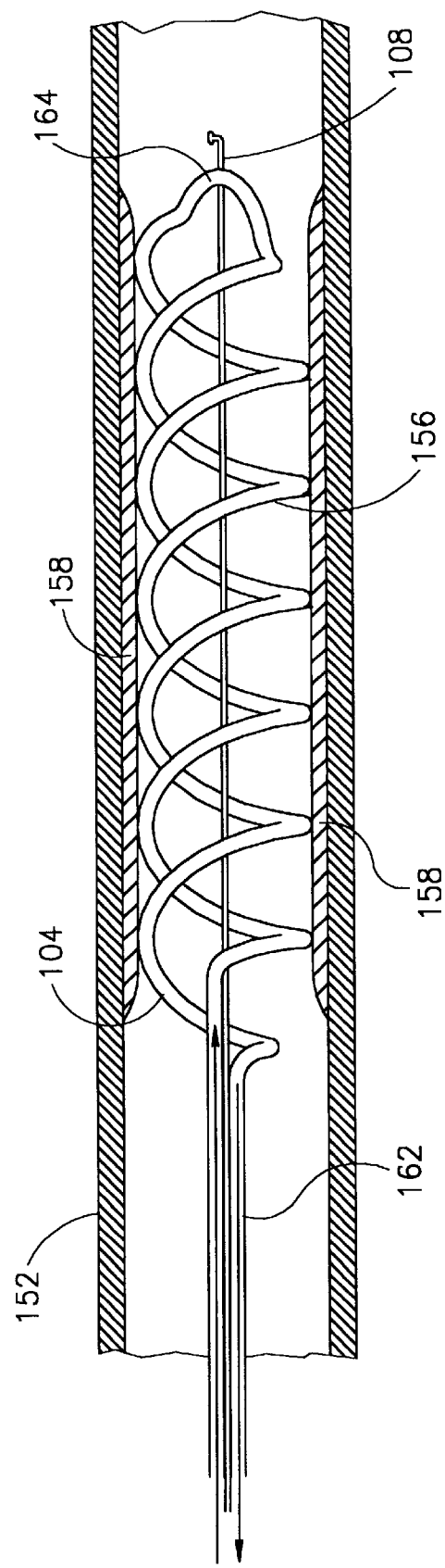
FIG.4A
FIG.4B

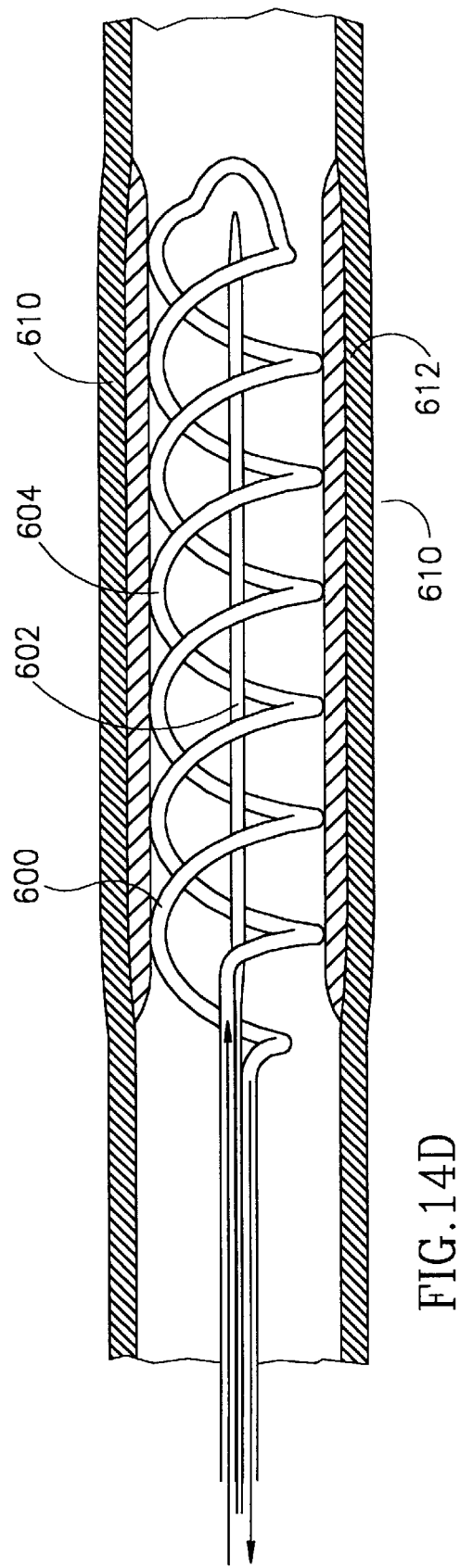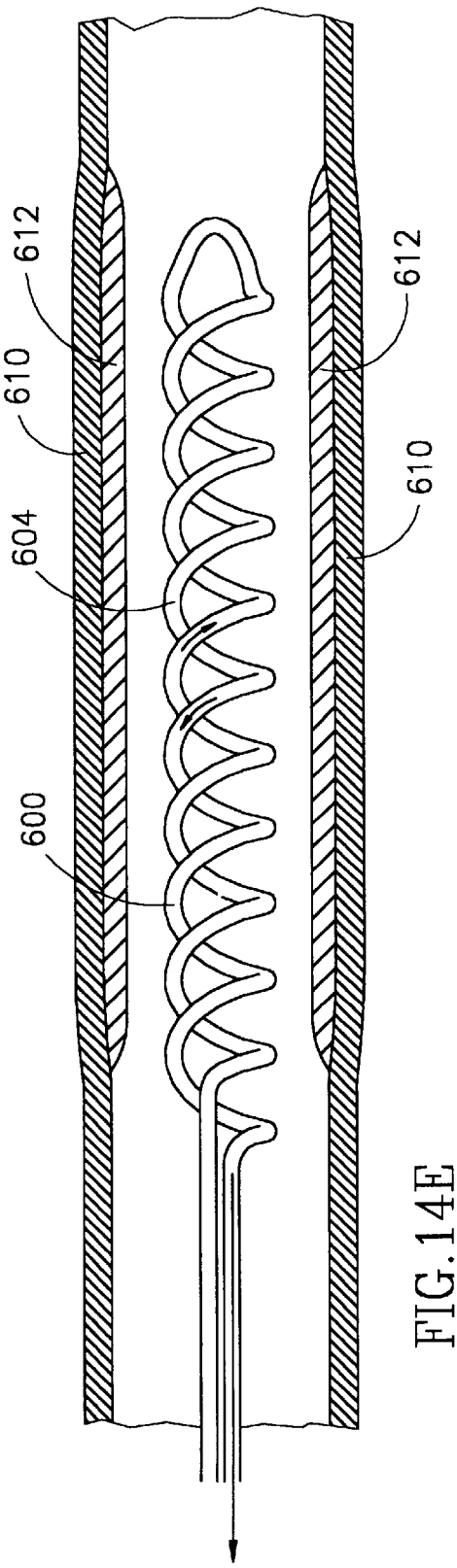
FIG.14D
FIG.14E

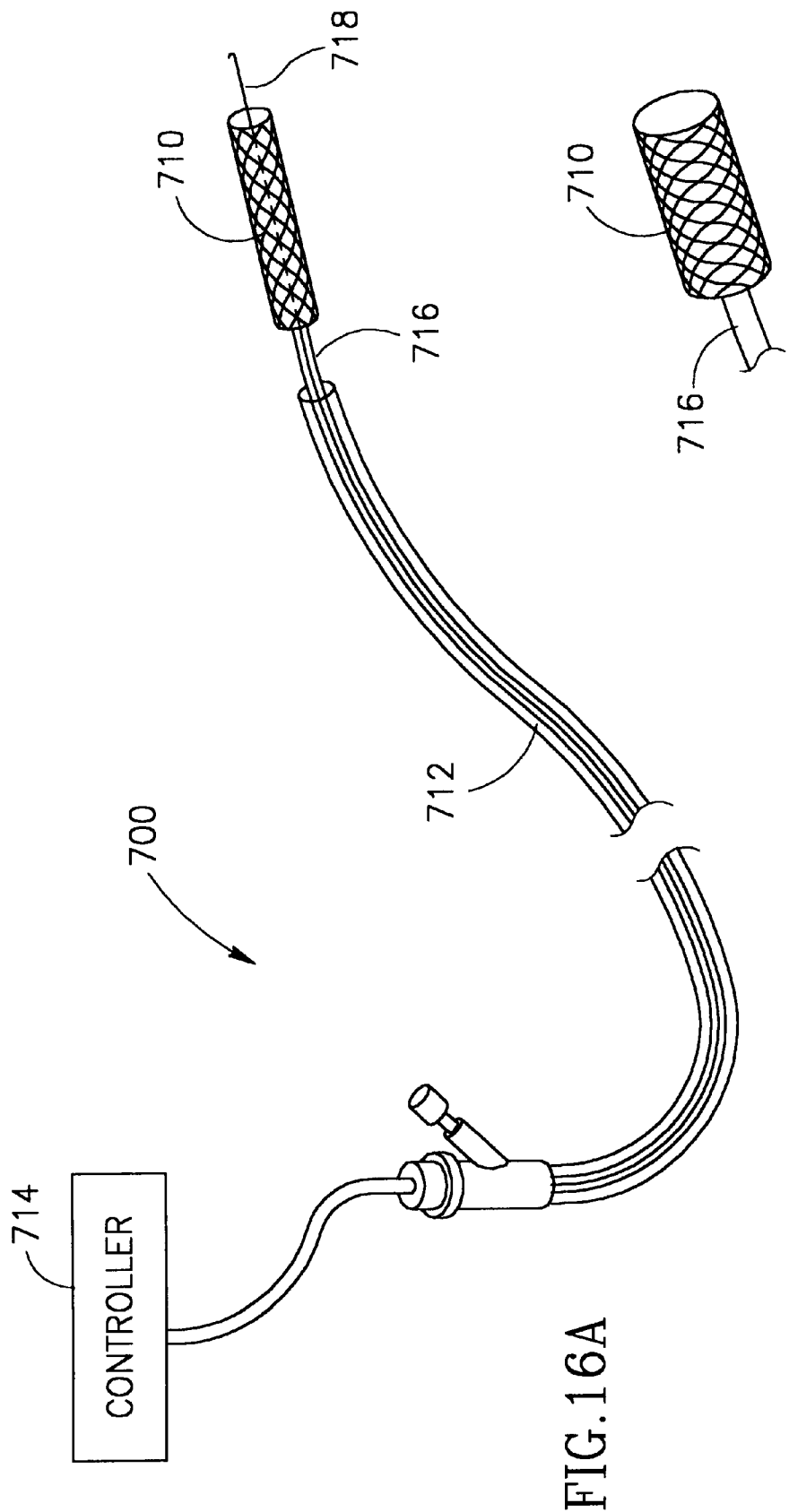

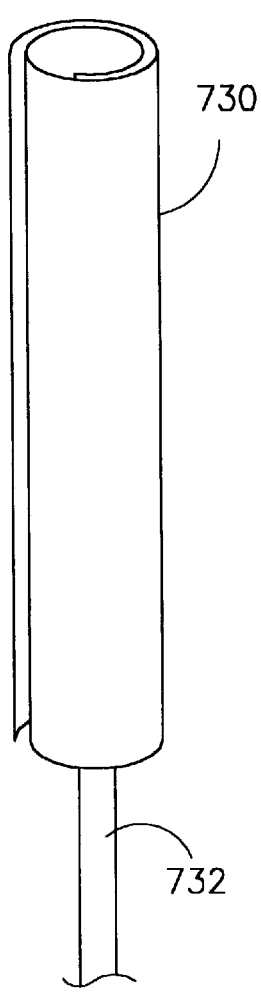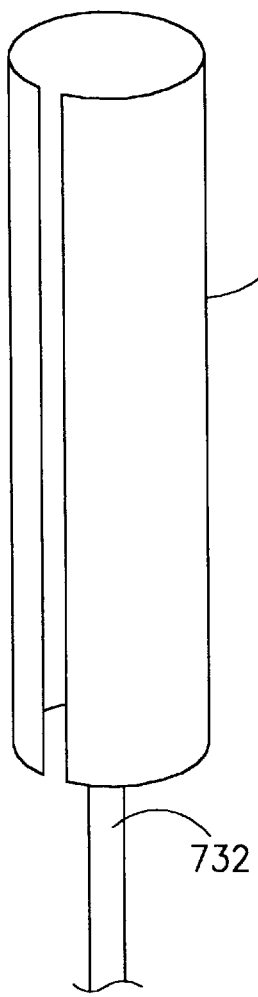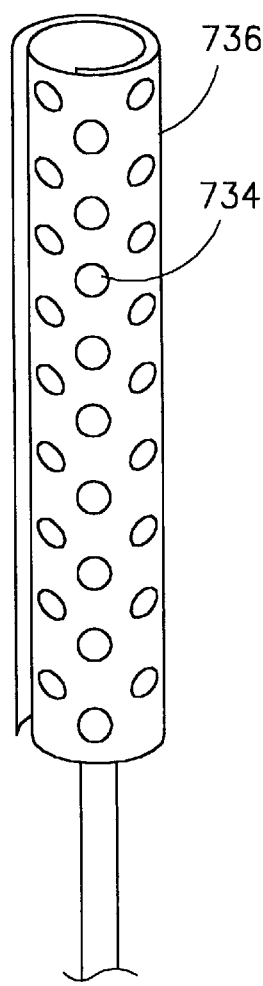
FIG.18A    FIG.18B    FIG.18E
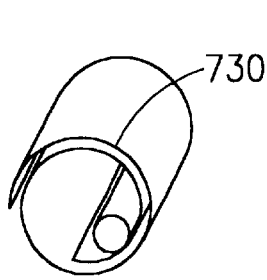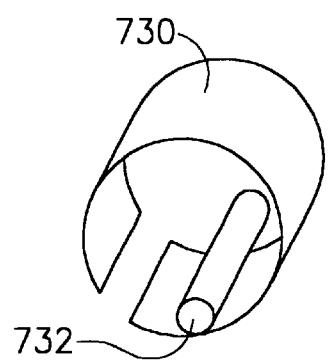
FIG.18C    FIG.18D

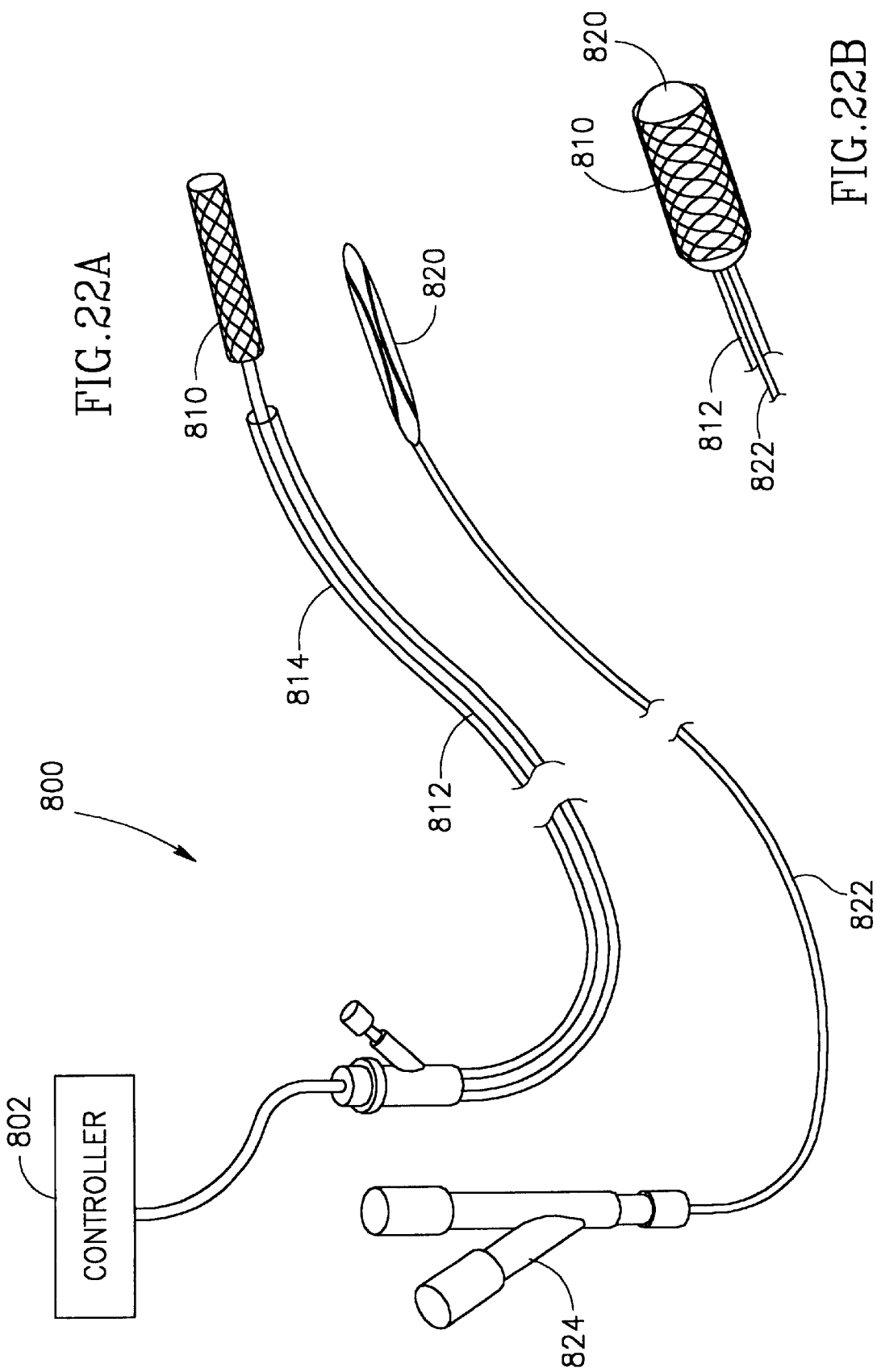

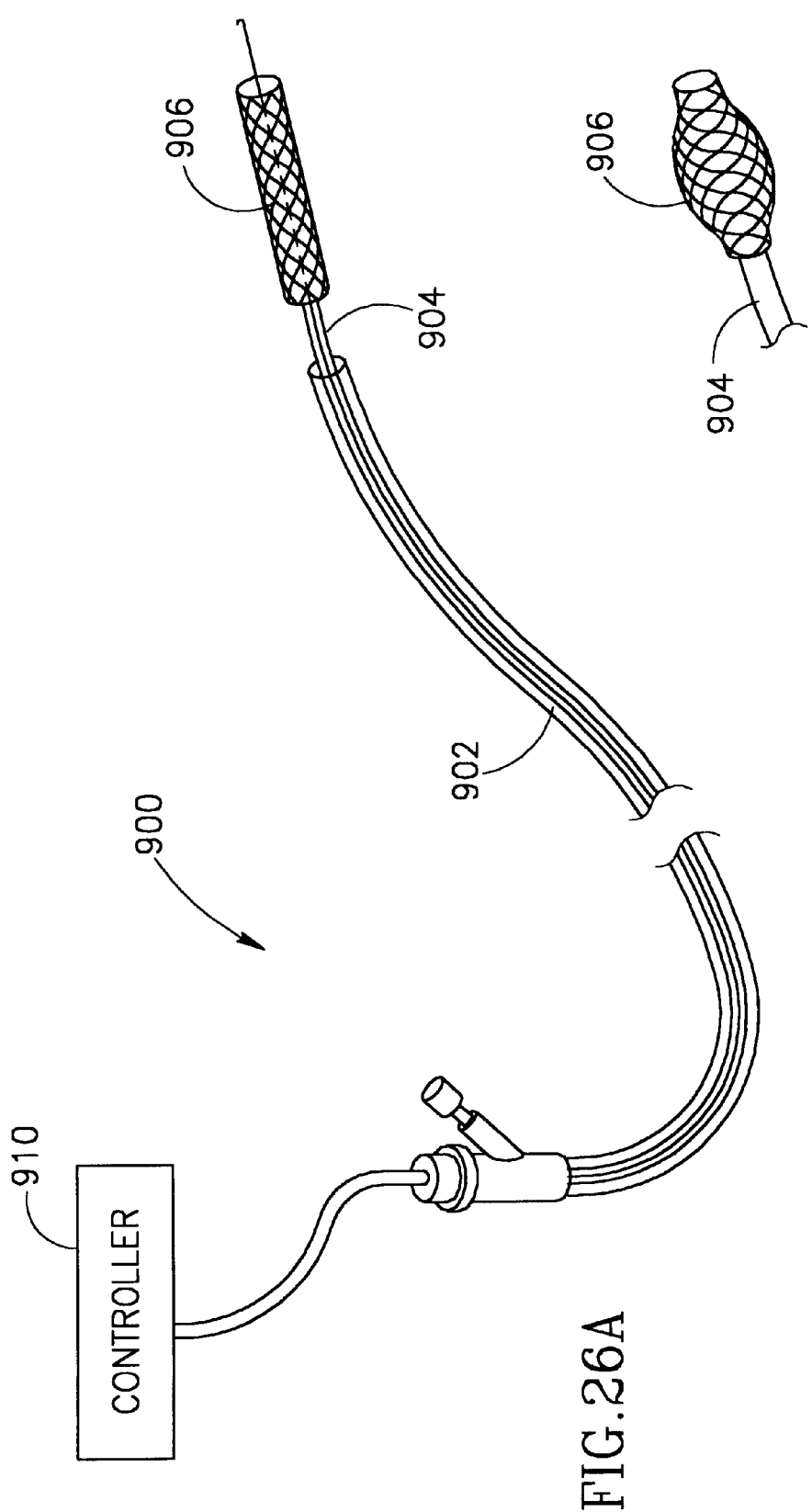

METHOD AND SYSTEM FOR TEMPORARILY SUPPORTING A TUBULAR ORGAN

CROSS-REFERENCE TO PREVIOUS APPLICATIONS

This application is a continuation-in-part of U.S. Ser. No. 09/274,851, now U.S. Pat. No. 6,258,118, a application entitled "REMOVABLE SUPPORT DEVICE", filed Mar. 23, 1999, which is a continuation-in-part of U.S. Ser. No. 09/199,556 a co-pending application entitled "CATHETER", filed Nov. 25, 1998.

FIELD OF THE INVENTION

The present invention relates to a method and a device for widening tubular organs in general and to a method and a device for widening arteries in particular.

BACKGROUND OF THE INVENTION

Devices and methods for widening tube shaped organs, in general and in the human body, in particular, are known in the art.

U.S. Pat. No. 5,716,410, to Wang et al, is directed to a catheter for vascular use. The catheter includes a directing mechanism and an inflatable balloon at the tip. The tip also includes a temporary stent, made of thermoplastic material. The catheter is inserted into the body of the patient, via a wide surface artery and the operator directs the catheter toward the destination location. When the tip is positioned at the destination location, then the operator pumps fluid to the balloon, via a tube, running along the catheter and starts inflating the balloon.

Reference is now made to FIG. 2, provided by Wang et al as FIG. 1, which is an illustration of a catheter, known in the art.

At the same time, the thermoplastic stent is heated, thereby unlocking its shape. The balloon, as it inflates, applies circumferencial pressure on the stent and the tubular organ, thereby forcing them to extend. Accordingly, the circumference of the tubular organ becomes larger. When the balloon brings the thermoplastic stent to the destination diameter, then the thermoplastic stent is cooled, thereby fixing its shape at a larger diameter, where it supports the tubular organ at an enlarged position.

Then, the operator reduces the pressure within the balloon, which in turn deflates and becomes smaller than the enlarged circumference of the tubular organ. The thermoplastic stent is then kept within the tubular organ for a time period which may range from a few minutes to as long as a week. Finally, the thermoplastic stent is reheated, thereby unlocking its shape, and enabling its removal from the body of the patient.

It will be appreciated by those skilled in the art, that a balloon is often longer than the segment to be treated. Hence, the inflatable portion of the balloon extends beyond the desired segments to healthy segments, and can cause damage thereto.

Furthermore, when a balloon is inflated inside a blood vessel, it occludes the blood flow distally and becomes a full barrier for any blood flow therein. It will be appreciated by those skilled in the art that many blood vessel related balloon treatments are performed in coronary arteries. Accordingly, such a procedure, while blocking blood flow through the treated blood vessel, may cause ischemia or even cardiac arrest.

The balloon blocks the blood flow both in the axial (through the blood vessel) and radial directions blocking branches.

The complete obstruction, a balloon related treatment is usually limited to one or two minutes of inflation, since the patient can not tolerate long time inflations, because of severe pain and chest discomfort, due to ischemia.

It will be appreciated by those skilled in the art that a blood vessel is generally a flexible organ. This fact, combined with the short time period in which a balloon expands the circumference of the blood vessel, (as much as 40% of the cases) causes the balloon treated blood vessel to assume its original size (recoil) immediately, or within few months shortly after the treatment.

A stent is generally an element, which is inserted into the tubular organ with the aid of a catheter. The initial shape of a stent is of an elongated cylinder, having a diameter, which is smaller than the narrowed section of the tubular organ, through which it has to pass. At the beginning of the treatment, the stent is positioned in the stenosed segment.

Then, the circumference of the stent is widened, by various methods, known in the art. One of these methods includes inserting a balloon into the stent and applying pressure by inflating it therewith. Accordingly, the stent widens, thereby applying pressure on the narrowed blood vessel. As a result, the stent widens the cross section of the diseased segment.

Finally, the balloon is deflated and is removed from the stent, which remains in its widened position, forcing the widened blood vessel to remain at its new state. Afterwards, the stent is covered by local tissue and is anchored thereto. This poses a disadvantage in the usage of a stent since such a stent can not be removed. A stent is an alien element within a living organism, which might produce thrombus in it.

In many cases (15%–40%) instant stenosis occurs. The mechanism of this narrowing is intimal proliferation thereby causing a new blockage at the same location. It is known by those skilled in the art that sometimes, such a reoccurring blockage is difficult to treat and in some cases, surgery is needed, to remove and replace the clogged section.

In some instances the stent may be lost and migrate distally in the coronary artery, or sometimes in the aorta and its branches. The stent also can be stuck.

Shape memory effect (SME) is a phenomena, in shape memory alloys (SMA) of a reversible transition from one solid phase into the other (i.e., from Martensite into Austenite or from Austenite to Martensite). Heating the alloy causes the transition from Martensite into Austenite. Cooling the alloy causes the reverse transition, from Austenite into Martensite. NiTi alloys are examples for such shape memory alloys.

Martensite and Austenite are two solid state phases, which are typical for alloys. Each of these phases is characterized in a certain crystalline structure.

Basically there are two types of shape memory effects. The first type is called the one way shape memory effect (OWSM), where the material transits from one of the above phase states to the other, only once. The second type is called the two-way shape memory effect (TWSM), where the material transits from one of the phase states to the other and back in a reversible process.

Shape memory alloys, such as Ni—Ti, Ni—Ti—X, Cu—Ni—Al, Cu—Zn—Al, Fe—Mn—Si, Ni—Ti—Co, Ni—Cu—X, Ni—Al and the like, are known in the art. These alloys exhibit a shape memory effect. In the Martensite condition, the shape alloy material is relatively flexible and soft, and can be easily deformed. When the material undergoes the transition into an Austenite state, it becomes more rigid, and is able to apply force and generate work, deform and enlarge the cross section of the blood vessel.

U.S. Pat. No. 5,540,713 to Shnepp-Pesch et al, is directed to an apparatus for widening a stenosis in a body cavity, also known as a shape memory stent. Shnepp-Pesch describes a stent made from a shape memory alloy, assuming a first predetermined shape at a first predetermined temperature and second predetermined shape at a second predetermined temperature. When heated from the first temperature to the second one, the shape memory stent changes its shape from a narrow generally cylindrical shape to a wider generally cylindrical shape.

Shnepp-Pesch describe a plurality of shapes which are applicable as shape memory stents. Reference is now made to FIGS. 1A–1H, provided by Shnepp-Pesch et al, as FIGS. 1A, 1B, 2A, 2B, 3A, 3B, 4A and 4B, respectively. These figures describe four shape memory stent structures, each at two states, one narrowed and the other enlarged.

It will be appreciated by those skilled in the art that this stent basically suffers the same disadvantages as any other stent, known in the art, as listed above.

SUMMARY OF THE PRESENT INVENTION

It is an object of the present invention to provide a system for opening and temporarily supporting generally tubular organs, in general and arteries in particular.

It is a further object of the present invention to provide a novel method for temporarily supporting a tubular organ, in general and vascular organs in particular.

In accordance with the present invention, there is thus provided a system for opening and temporarily supporting a section of a generally tubular organ. The system includes a dilation catheter. The dilation catheter includes an integrally connected shape memory catheter tip. The shape memory catheter tip is made of a shape memory alloy, wherein the shape memory catheter tip assumes a first shape at a first temperature and a second shape at a second temperature. It is noted that the shape memory catheter tip is generally hollow, thereby enabling flow of bodily fluid there through.

The system can further include an energy control unit, connected to the dilation catheter, and an energy transfer unit. The energy control unit controls the temperature of the shape memory catheter tip. The energy transfer unit is connected between the shape memory catheter tip and the energy control unit, and generally located within the dilating catheter, for transferring energy there between.

The shape memory catheter tip can include a plurality of shapes. For example, the shape of the shape memory catheter tip can be selected from the list consisting of a generally cylindrical coil, a generally cylindrical mesh, a folded foil and the like. Such a folded foil can include a plurality of openings.

According to one aspect of the invention, the first shape is generally the shape of a cylindrical coil, having a first diameter and wherein the second shape is generally the shape of a cylindrical coil, having a second diameter. According to another aspect of the invention, the first shape is generally the shape of a cylindrical mesh having a first diameter and wherein the second shape is generally the shape of a cylindrical mesh having a second diameter. According to a further aspect of the invention, the first shape is generally the shape of a cylindrically folded foil having a first diameter and wherein the second shape is generally the shape of a cylindrically folded foil having a second diameter.

The energy transfer means can include at least one conduit. Such conduits can include concentric conduits. The temperature control unit can include means for providing temperature-controlled fluid towards the shape memory unit via the energy transfer means. The conduit can be opened in the vicinity of the shape memory catheter tip, thereby releasing temperature controlled fluid in the vicinity of the shape memory catheter tip. The temperature control unit can further be connected electrically to the shape memory unit, thereby electrically heating the shape memory unit from the first temperature to the second temperature.

The energy transfer means can further include an electricity-conducting unit, connected electrically to the shape memory unit. Accordingly, the temperature control unit can include an electric power supply unit, for electrically heating the shape memory unit from the first temperature to the second temperature.

It is noted that the first temperature can be set to be equal or below the temperature of the environment, in which the shape memory catheter tip is placed. The shape memory alloy can be selected from the list consisting of: Ni—Ti, Ni—Ti—X, Cu—Ni—Al, Cu—Zn—Al, Fe—Mn—Si, Ni—Ti—Co, Ni—Cu—X, Ni—Al and the like.

For example, the first temperature can be in the range of 5 degrees Celsius and 38 degrees Celsius. Alternatively, the first temperature is in the range of 20 degrees Celsius and 38 degrees Celsius. Similarly, the second temperature can be in the range of 36 degrees Celsius and 65 degrees Celsius. Alternatively, the second temperature is in the range of 36 degrees Celsius and 50 degrees Celsius.

According to another aspect of the invention, the shape memory unit includes a generally cylindrical hollow coil, having an inlet and an outlet and the temperature transfer means includes two conduits. Accordingly, one of the conduits is connected to the inlet of the shape memory unit for introducing the fluid thereto, and the other of the conduits is connected to the outlet, for receiving the fluid therefrom.

According to a further aspect of the invention, the system further includes elastic elements, such as a spring, attached to the shape memory catheter tip having an initial shape, wherein the initial shape (of the elastic elements) is generally similar to the first shape (of the catheter tip). The elastic elements apply force on the shape memory catheter tip so as to deform the shape memory catheter tip to the initial shape. The elastic elements can be attached to the shape memory unit.

The front section of the shape memory catheter tip can be shaped as a guiding front end. Alternatively, the system can further include a guiding unit having a guiding tip, wherein the guiding unit is located within the dilation catheter and extends beyond the shape memory catheter tip. The guiding tip can be operable to move relative to the shape memory catheter tip.

It is noted that according to one aspect of the invention, the first diameter can be smaller than the second diameter. Alternatively, the first diameter can be larger than the second diameter.

The shape memory catheter tip enables flow of bodily fluid in a radial direction and in an axial direction, by having front, rear and side openings.

In accordance with another aspect of the invention, the system can further includes an inflatable balloon. The balloon is operative to inflate, thereby changing the shape memory catheter tip from the first shape into the second shape. According to this aspect, the shape memory catheter tip changes from the second shape to the first shape when heated from the first temperature to the second temperature.

In accordance with a further aspect of the invention, there is provided a method for operating the system including the steps of: inflating the balloon, thereby increasing the diameter of the shape memory catheter tip, deflating the balloon, thereby enabling flow of bodily fluids through the shape memory catheter tip, heating the shape memory catheter tip to a predetermined temperature, thereby moving the shape memory catheter tip to an Austenite state which decreases the diameter of the shape memory catheter tip.

The method can further include a preliminary step of locating the shape memory catheter tip and the balloon in a selected area within a generally tubular organ. The method can further include a further preliminary step of inserting the shape memory catheter tip and the balloon into the body of the patient. Moreover, the method can further include a step of removing the shape memory catheter tip from the selected area.

BRIEF DESCRIPTION OF THE DRAWINGS

The present invention will be understood and appreciated more fully from the following detailed description taken in conjunction with the drawings in which:

FIGS. 1A–1H, are schematic illustrations of a tubular restraining devices, which are known in the art;

FIGS. 4A and 4B are illustrations of the tip end of the device of FIG. 3, constructed and operative in accordance with another preferred embodiment of the present invention;

FIGS. 14B, 14C, 14D, 14E and 14F are illustrations of parts of the system of FIG. 14A;

FIGS. 16A and 16B are illustrations of a catheter system, constructed and operative in accordance with a further preferred embodiment of the present invention;

FIGS. 18A, 18B, 18C, 18D and 18E are illustrations of an alternative catheter tip, constructed and operative in accordance with another preferred embodiment of the invention;

FIG. 22A is a schematic illustration of a catheter system, constructed and operative in accordance with another preferred embodiment of the present invention;

FIG. 22B is an illustration in detail of a portion of the system of FIG. 22A;

FIG. 26A is a schematic illustration of a catheter system, constructed and operative in accordance with another preferred embodiment of the present invention;

FIG. 26B is an illustration in detail of a portion of the system of FIG. 26A;

DETAILED DESCRIPTION OF PREFERRED EMBODIMENTS

The present invention overcomes the disadvantages of the prior art by providing a novel device which is a catheter, having a hollow SMA element as its tip.

Furthermore, the present invention provides a novel method for operating the device of the invention, which overcomes the disadvantages of the prior art.

Figure 2:
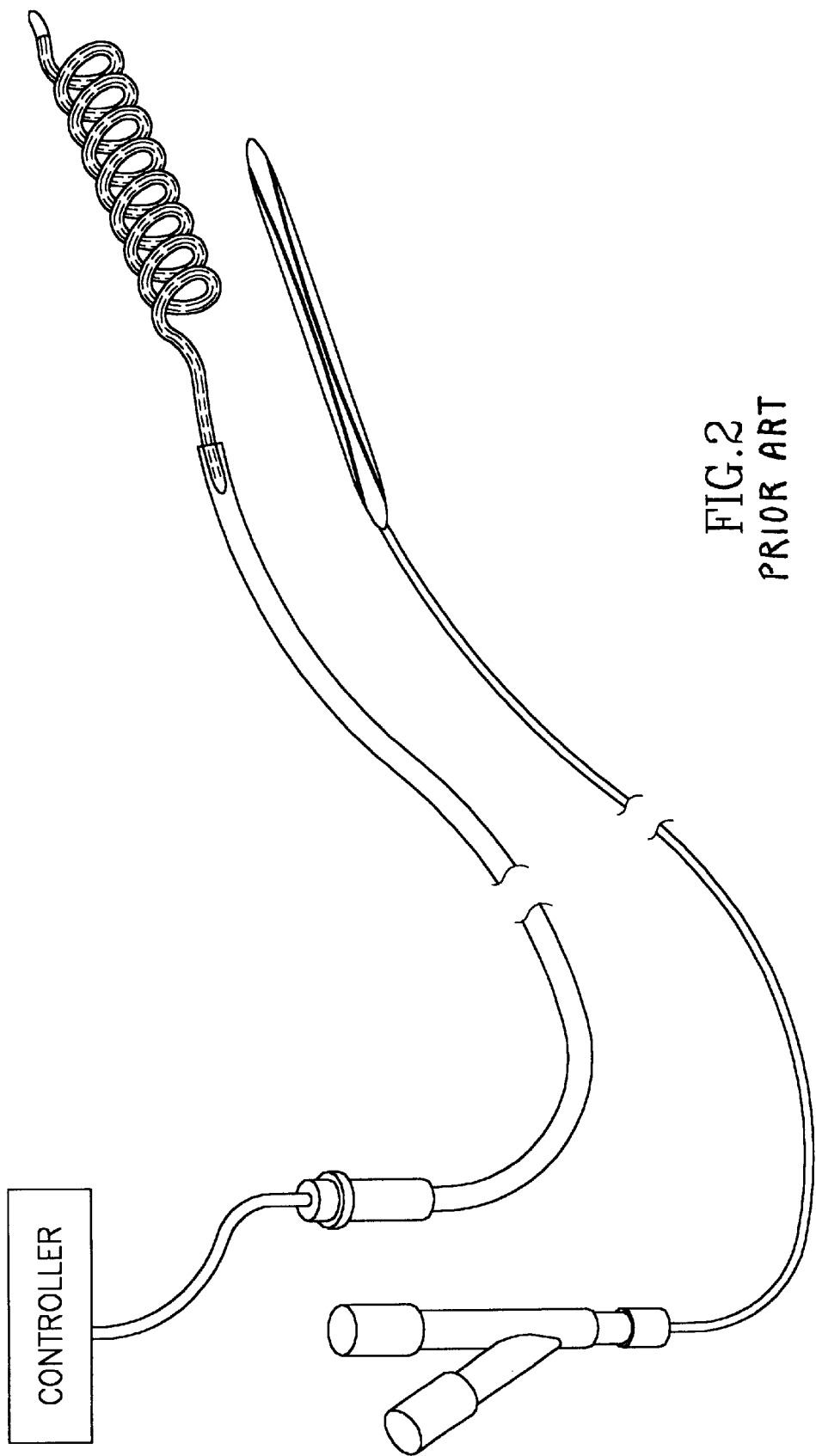
FIG. 2 is a schematic illustration of a catheter having a balloon as its tip, which is known in the art.
Figure 3:
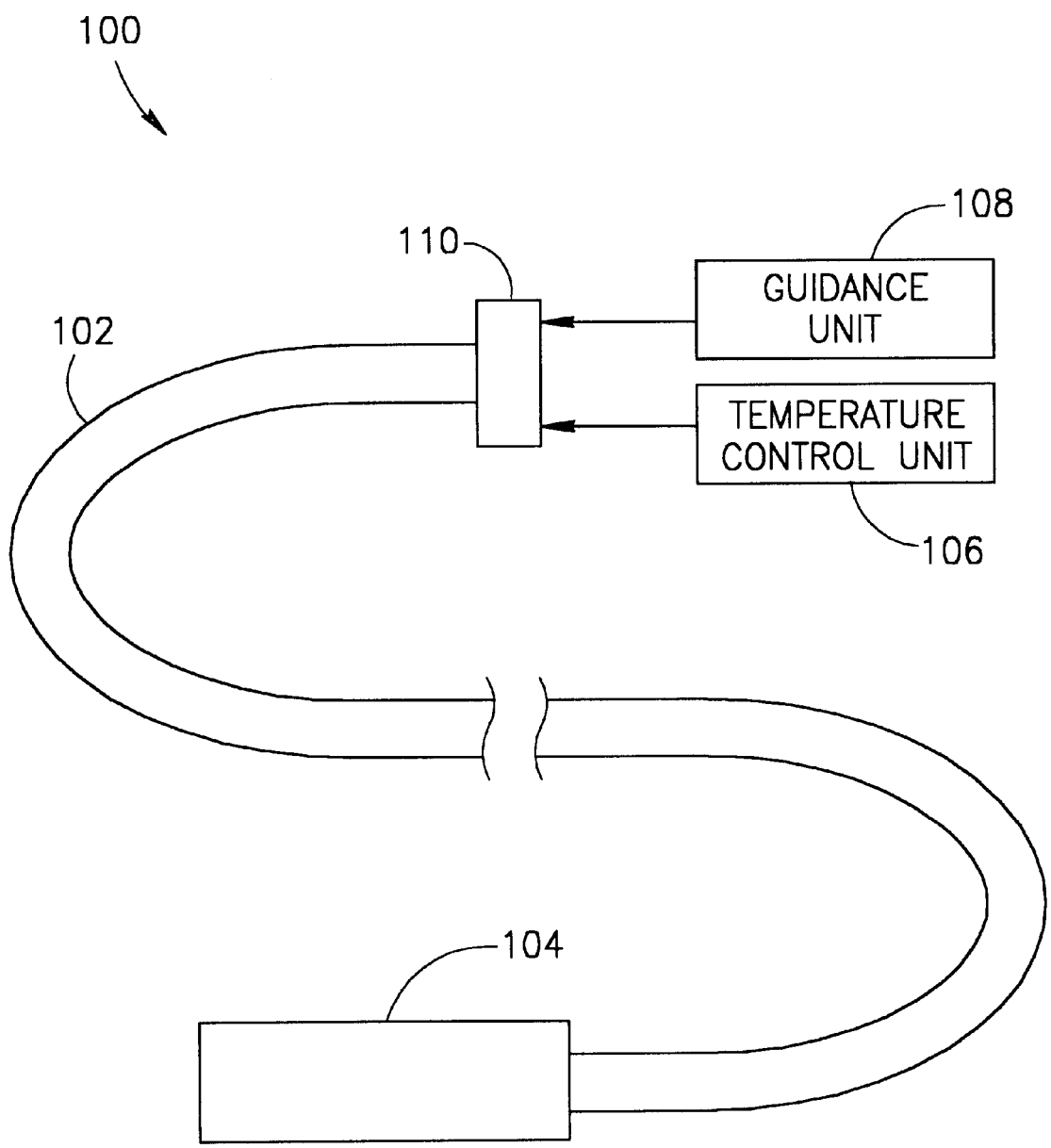
FIG. 3 is a schematic illustration of a device for treating a tubular organ, constructed and operative in accordance with a preferred embodiment of the invention.

Reference is now made to FIG. 3 which is a schematic illustration of a device, generally referenced 100, for treating a tubular organ, constructed and operative in accordance with a preferred embodiment of the invention.

The device 100 includes a guiding catheter 102, a "Y" connector 110, a hollow SMA tip 104, a guidance unit 108 and a fluid supply and temperature control unit 106.

The guide wire 108 is inserted through guiding catheter 102 via the "Y" connector 110. The temperature control unit is connected to the Hollow SMA tip, which is inserted via the "Y" connector 110, and over the guide wire 108.

The guiding catheter 102 is an elongated tubular element which guides and locates the tip 104 within the patients tubular organ, which for example, can be a blood vessel, a urether, urethra, bile duct, colon eosophagus, stenosed valve, etc. and the like. The user of the device 100, which is a medically trained person, uses the guidance Wire 108 to insert over it SMA tip into the diseased segment.

Reference is also made now to FIGS. 4A and 4B, which are illustrations of the tip end of the device 100, of FIG. 3. FIG. 4A shows the tip 104 inserted into a blood vessel 152, having a section 158, which is relatively narrower than the rest of the blood vessel.

The tip 104 includes a hollow shaped SMA element which is adapted to perform a transition from one shape at a first predetermined temperature range to another shape, at a second predetermined temperature range.

In the present example, the tip includes a helical SMA element 156. The helical SMA element 156 has a narrow circumference shape at a temperature, which is equal or lower to a first temperature value $T_1$, as shown in FIG. 4A. The helical SMA element 156 has a wide cross section shape at a temperature, which is equal or higher to a second temperature value $T_2$, as shown in FIG. 4B.

The helical SMA element 156 is inserted over the guide wire 108 through guiding catheter 102 (FIG. 3). It is shaped so that its front end 164 (FIG. 4) has a round shape, which is designed so that no damage is inflicted onto the blood vessel through which the tip is inserted. At its other end 162, the helical SMA element 156 is connected to hollow tubes, which are able to supply various fluid temperatures thereon (shown in detail in conjunction with FIG. 8).

The device 100 is used to expand the circumference of the blood vessel 152, at its narrowed cross section 158, using the SMA tip 104.

Accordingly, the user inserts the SMA element 156 into the blood vessel 152 and positions it in the diseased segment 158. It is noted that all through the insertion phase, the helical SMA element 156 is maintained at a temperature, which is not higher than $T_1$, thereby assuming its narrowed form.

When the helical SMA element 156 is located within the diseased section 158, then, the user operates the temperature control unit 106, which heats the helical SMA element 156 to a temperature, which is not lower than $T_2$. As the helical SMA element 156 heats, it undergoes a transition from its narrow shape into its wider shape. Accordingly, the helical SMA element 156 applies circumferencial pressure on the diseased segment 158, thereby forcing it to become wider (FIG. 4B).

According to the present invention, the user can maintain the helical SMA element 156 at its position, for a considerable period of time, which is in the order of minutes, hours and days, as needed.

As the shape of the helical SMA element 156 does not block flow. No ischemia is produced and hence, no harm or suffer is inflicted onto the patient, during this time period.

After reducing the SMA element 156 to its' original size, the physician can direct it to another location, within the artery and use it again. Accordingly, the device of the present invention can be used for a plurality of narrowed artery locations, one after the other, without the need to remove the catheter out of the body of the patient.

According to the present invention, the heating up and cooling down of the helical SMA element 156 can be performed in a plurality of ways such as inducing a temperature bearing fluid there through, electric current, radiation, induction heating, and the like.

According to one aspect of the present invention, the helical SMA element 156 is made of a hollow wire, through which temperature bearing fluid is induced or others.

As the diseased segment 158 is forced to be in a widened state (FIG. 4B) for a considerable time, by the helical SMA element 156, then the probability of it shrinking back to its narrow state (FIG. 4A) decreases significantly.

At the end of the treatment, the user, operates the temperature control unit 106, to lower the temperature of the helical SMA element 156, which in turn returns to its initial state as shown in FIG. 4A. Finally, the user takes out the SMA catheter 100 than the guide wire 108 and finally the guiding catheter 102 out of the body of the patient, or to another vessel, which needs to be dilated.

It will be noted that according to this aspect of the present invention, no element such as a stent, remains in the artery, to maintain its widened state, at the end of the treatment. Hence, at any time after the treatment, any type of catheter can be inserted into the artery, passing distally through section 158, for example, for repeating the treatment of section 158.

According to the present invention, the helical SMA element 156 is made of a hollow conduit. A fluid flowing there through having a predetermined temperature, applies that temperature thereon. Accordingly, a temperature change can be applied on the element 156.

The side walls of the catheter are substantially round shaped having a smooth surface, for reducing the probability of inflicting any damage to the inside walls of the treated artery (the intima).

Reference is now made to FIGS. 5A, 5B, 5C, 5D and 5E, which are illustrations of cross sectional variations for helical SMA element 156, constructed and operative in accordance with the present invention.

Figure 5A:
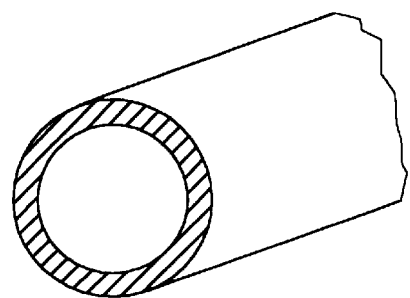
FIGS. 5A, 5B, 5C, 5D and 5E are illustrations of typical cross sectional variations for helical SMA element of FIGS. 4A and 4B.
Figure 5B:
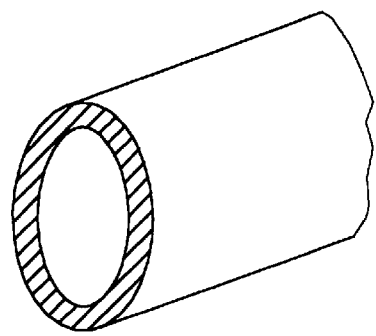
Figure 5C:
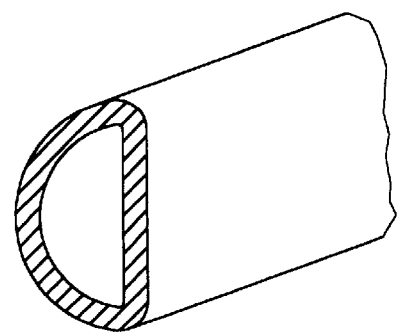
Figure 5D:
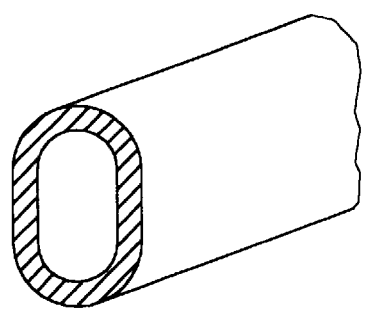
Figure 5E:
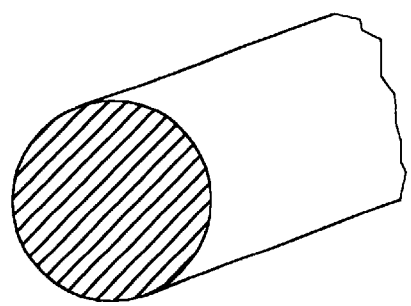

FIG. 5A shows a circular cross section, FIG. 5B shows an elliptical cross section, FIG. 5C shows a half elliptical cross section, FIG. 5D shows a near rectangle cross section and FIG. 5E shows a solid (full) radial cross section.

Figure 6:
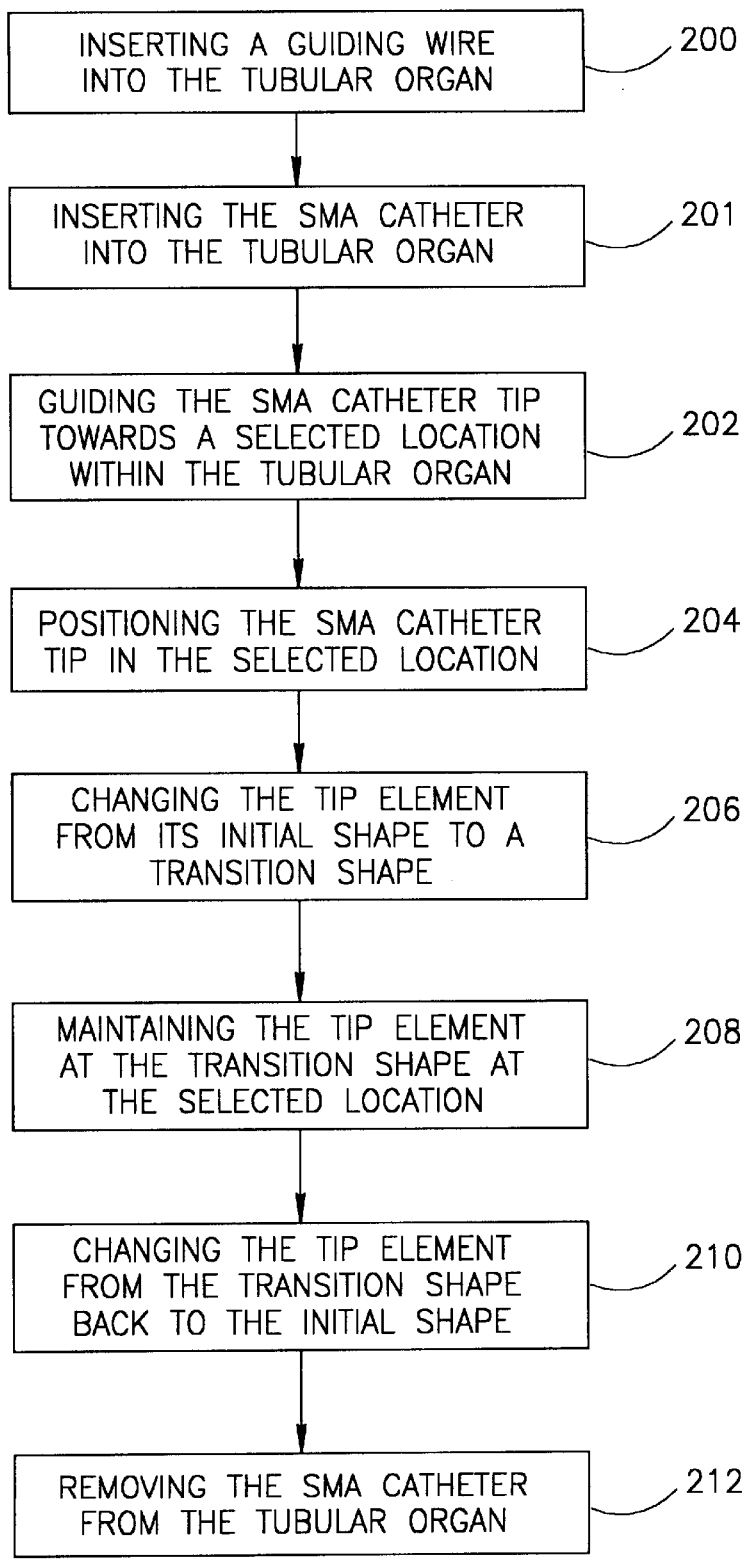
FIG. 6 is a schematic illustration of a method for operating the device of FIG. 3, operative in accordance with another preferred embodiment of the present invention.

Reference is now made to FIG. 6, which is a schematic illustration of a method for operating the device 100 of FIG. 3, operative in accordance with another preferred embodiment of the present invention.

In step 200, a guiding wire is inserted into the tubular organ within the body of the patient, and is guided into the section to be treated. This tubular organ can be, for example, a blood vessel, a urether, a urethra, bile duct, colon, eosophagus, stenosed valve, and the like. In the case of a blood vessel, the guiding tip can be inserted from a peripheral artery.

In step 201, the device 100, which is an SMA catheter is inserted into the tubular organ, guided via the guiding wire towards the section to be treated.

In step 202, the device 100 is guided through the tubular organ towards a selected location, which is a portion of the tubular organ, which is narrower than as it should be and need to be widened. In the present example, there is a blockage in this location caused by atherosclerosis.

In step 204, the user, which is part of the medical stuff treating the patient, positions the tip of the SMA catheter in the selected location. The SMA element can be heated by fluid, electric current, radiation, induction heating, and the like.

In step 206, the SMA tip of the device 100 changes from an initial shape to a transition shape. This can be done by means of a phase transition, which can be caused by a temperature change (increase). Being in the transition shape, the SMA tip applies circumferencial pressure on the walls of the selected section, thereby forcing it to increase its circumference (208). The tip is maintained in this position and shape, so as to reduce the probability of the selected section returning to its original circumference shortly after the treatment is ended.

In step 210, the tip element is changed from the transition shape back into the initial shape. This is done by means of a phase transition, which is caused by a temperature change (decrease).

In step 212, the device 100 is removed from the tubular organ. It will be noted that the device 100, can remain in the body of the patient for a subsequent treatment of another such section.

It is noted that according to the present invention blood flow is maintained throughout the treatment and the device, according to the invention, does not block blood flow neither in the axial direction, nor in the radial direction. Accordingly, the method of the present invention is applicable for patients, which may not endure a blood blocking balloon treatment.

Since the device of the present invention is completely removed from the body of the patient and leaves no object therein, then, the probability of intimal proliferation in the treated segment, is significantly reduced.

It is noted that the method of the present invention enables the physician to treat conical shaped segment by using conical SMA tip.

Figure 7:
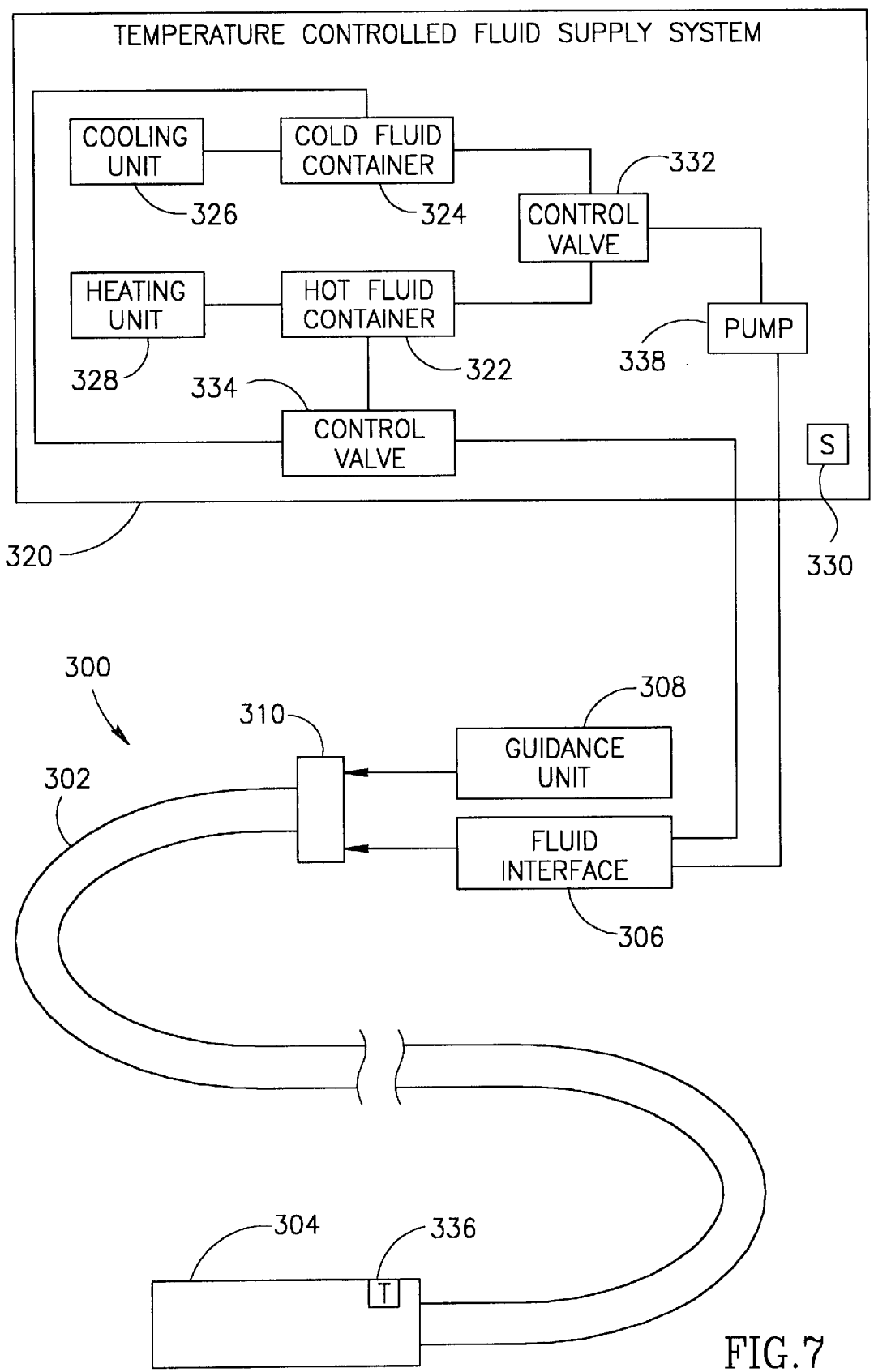
FIG. 7 is a schematic illustration of a system, constructed and operative in accordance with a further embodiment of the present invention.

Reference is now made to FIG. 7, which is a schematic illustration of a system, generally referenced 300, constructed and operative in accordance with a further embodiment of the present invention.

System 300 includes a catheter assembly 302, a guidance unit 308, a fluid connector 306 and a temperature control system 320.

The catheter assembly 302 includes a tip 304, a temperature sensor 336 for sensing the temperature of the treated area as well as the temperature of the tip 304 and a quick release interface 310. It is noted that the addition of temperature sensors is an option, provided by the invention. This addition enhances the control and accuracy of the temperature of the fluid and hence, the temperature of the SMA tip 304.

The guidance unit 308 enables the physician to guide the tip of the catheter 302, towards the target area to be treated.

The fluid connector 306 enables the physician to supply variable fluid temperature and flow into the catheter 302, and the like.

The temperature control system 320 provides a continuous supply of fluid according to the specification, received from the user via connector 306.

The temperature control system 320 includes a pump 338, a hot fluid container 322, a cold fluid container 324, a cooling unit 326, a heating unit 328, control valves 332 and 334 and a sensor 330.

The cooling unit 326 is connected to the cold fluid container 324. The hot fluid container 322 is connected to the heating unit 328 and to the control valves 332 and 334. The control valve 332 is connected between the pump 338 and both containers 324 and 322.

The pump 338 is further connected to the fluid connector 306, which is further connected to the control valve 334.

The cooling unit 326 cools the fluid, which is contained in the cold fluid container 324. The heating unit 328 heats the fluid, which is contained in the hot fluid container 322. The control valve 332 directs fluids received from the cold fluid container 324 and the hot fluid container 322 and provides the fluid to the pump 338.

The pump 338 provides a fluid at a controlled pressure to the fluid interface 306. This fluid flows towards the tip 304 thereby applying its temperature, thereon (i.e., when the temperature of the fluid is greater than the temperature of the tip, then the tip will be heated up and when the temperature of the fluid is lower than the temperature of the tip, then the tip will cool down).

After modifying the temperature of the tip 304, the fluid flows back to the temperature control system 320, via the fluid connector 306, to be stored in the containers. The control valve 334 provides fluid to the containers 322 and 324.

The fluid sensor 330 monitors the fluid at the output of the pump 338, thereby providing data relating to the temperature and pressure of the fluid. This data is used to control the pump 338 and the heating element 328 and the cooling element 326.

It is noted that the catheter assembly 302, can also conduct fluid, directly therethrough, and release it in the vicinity of the tip. Accordingly, the tip can be made of a wire, which has a solid cross-section.

Figure 8:
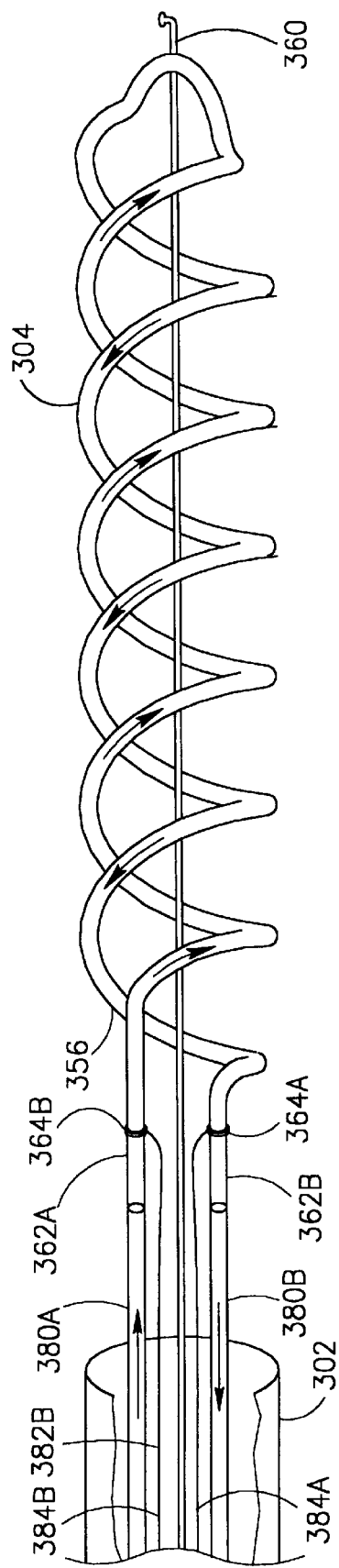
FIG. 8 is a schematic illustration in detail of the connection section of a helical SMA element and the inner side of the guiding catheter.

Reference is further made to FIG. 8, which is a schematic illustration in detail of the connection section of a helical SMA element 356 and the inner side of the guiding catheter 302 (FIG. 8). The helical SMA element 356 includes an inlet 362A and an outlet 362B, which are connected to a fluid inlet conduit 380A and a fluid outlet conduit 380B. The fluid inlet conduit 380A is connected to the inlet 362A, while the fluid outlet conduit 380B is connected to the outlet 362B. Temperature controlled fluid, provided by system 320, is provided to the helical SMA element 356 via the inlet fluid conduit 380A. After modifying the temperature of the helical SMA element 356, the fluid exits via the outlet fluid conduit 380B. It is noted that a guiding wire 360 is inserted through the guiding catheter 302 to the end of the tip 304.

According to the present example, the helical SMA element 356 is alternatively connected to two electrically conducting wires 384A and 384B, via electrical contacts 364A and 364B, respectively. These wires provide a flow of electrical current via the metal body of the helical SMA element 356, thereby heating it. According to this example, the heating is performed electrically, while the cooling can be performed either by setting the reduced diameter temperature to the body temperature of the patient or by introducing cooled fluid via conduits 380A and 380B.

Figure 9:
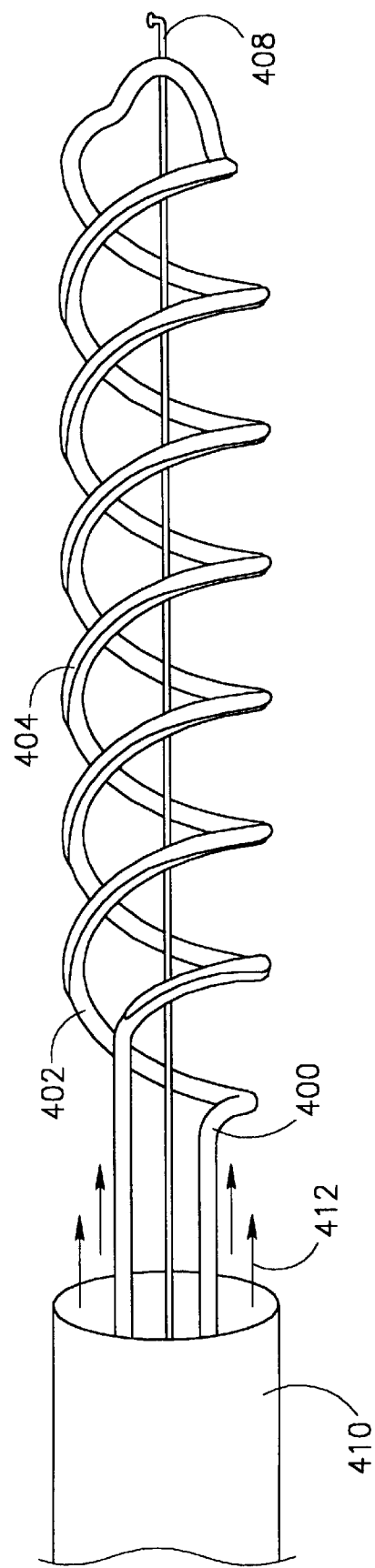
FIG. 9 is a schematic illustration in detail of a catheter tip, constructed and operative in accordance with another preferred embodiment of the present invention.

Reference is now made to FIGS. 9, 10A, 10B, 10C, 10D, 10E, 10F and 10G. FIG. 9 is a schematic illustration in detail of a catheter tip, generally referenced 400, constructed and operative in accordance with another preferred embodiment of the present invention. FIGS. 10A, 10B, 10C, 10D, 10E, 10F and 10G are illustrations of cross sectional variations for catheter tip 400, which include auxiliary elastic means.

Catheter tip 400 includes a helical SMA element 402, and a helical elastic element 404, attached thereto. SMA element 402 is generally similar to elements 104 and 304.

According to one aspect of the invention, the helical elastic element 404 is inserted within helical SMA element 402, as illustrated in FIGS. 10A, 10B, 10C, 10D and 10E. According to a further aspect of the invention (FIGS. 10F and 10G), the helical elastic element 404 is attached to the outer surface of helical SMA element 402.

Figure 10A:
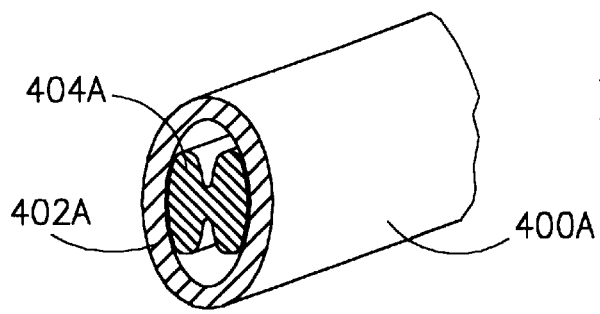
FIGS. 10A, 10B, 10C, 10D, 10E, 10F and 10G are illustrations of typical cross sectional variations for the catheter tip of FIG. 9.

FIGS. 10A is a cross sectional illustration of a variation of SMA element 402, which includes a hollow helical SMA element 402A having an elliptic cross section and a helical elastic element 404A having an "I" cross section.

Figure 10B:
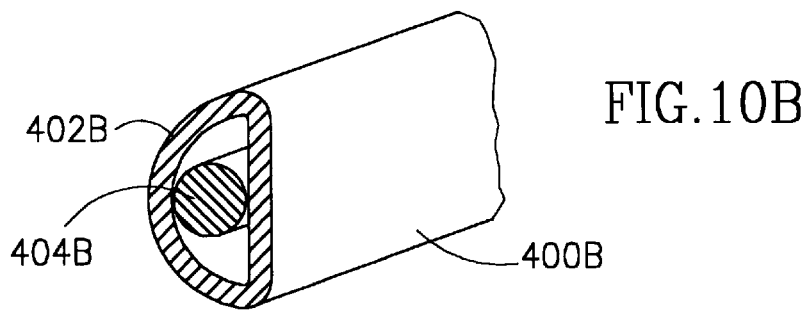

FIGS. 10B is a cross sectional illustration of a variation of SMA element 402, which includes a hollow helical SMA element 402B having a semi-elliptic cross section and a helical elastic element 404B having a radial cross section.

Figure 10C:
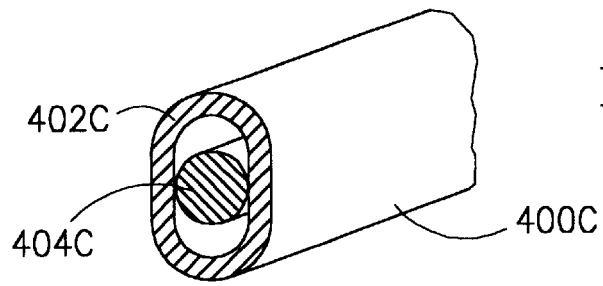

FIG. 10C is a cross sectional illustration of a variation of SMA element 402, which includes a hollow helical SMA element 402C having a near rectangle cross section and a helical elastic element 404C having a radial cross section.

Figure 10D:
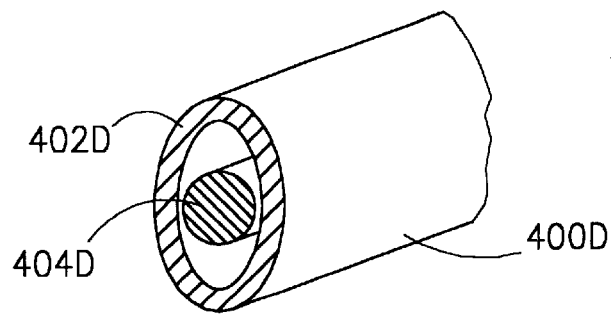

FIG. 10D is a cross sectional illustration of a variation of SMA element 402, which includes a hollow helical SMA element 402D having an elliptic cross section and a helical elastic element 404D having a radial cross section.

Figure 10E:
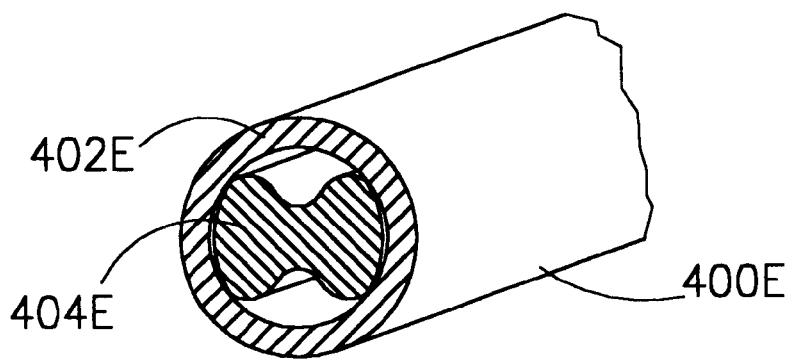

FIG. 10E is a cross sectional illustration of a variation of SMA element 402, which includes a hollow helical SMA element 402E having a radial cross section and a helical elastic element 404E having an "I" shaped cross section.

Figure 10F:
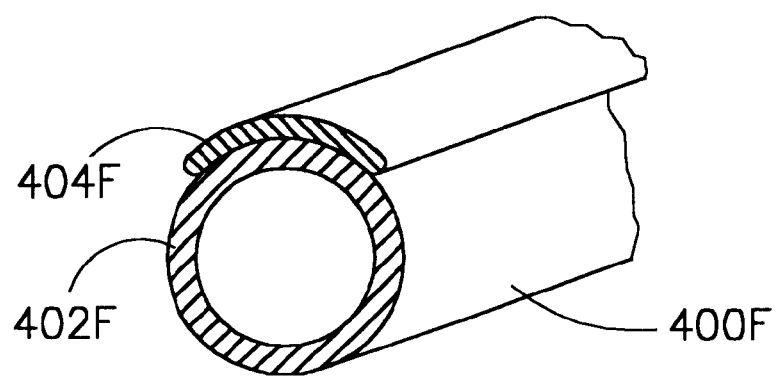

FIG. 10F is a cross sectional illustration of a variation of SMA element 402, which includes a hollow helical SMA element 402F having a radial cross section and an external elastic element 404F.

Figure 10G:
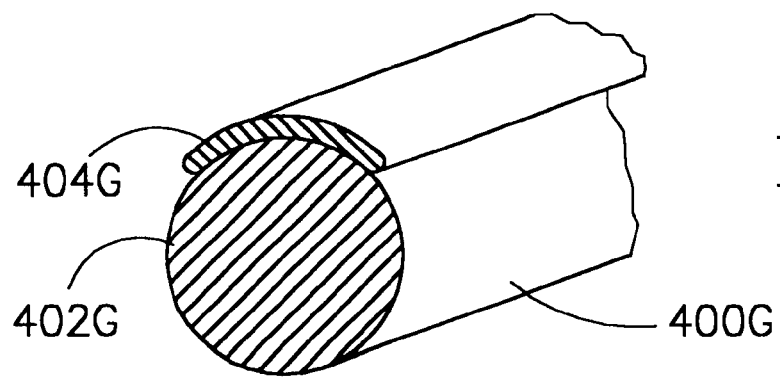

FIG. 10G is a cross sectional illustration of a variation of SMA element 402, which includes a solid (full) helical SMA element 402G having a radial cross section and an external elastic element 404G.

The helical SMA element 402 has a narrow circumference shape at a temperature, which is equal to or lower than a first temperature value $T_1$. The helical SMA element 402 has a wide circumference shape at a temperature, which is equal to or higher than a second temperature value $T_2$.

The helical elastic element 404 has a narrow diameter shape, which is in the order of the narrow diameter shape of the helical SMA element 402.

It is noted that the helical elastic element 404 can be deformed to a different shape, by an external force and return back by itself, to its original narrow circumference shape.

According to the present invention, the catheter tip 400 performs a transition from the narrow circumference shape to a wide circumference shape, by heating the helical SMA element 402 beyond predetermined temperature $T_2$. At this stage, the helical SMA element 402 is in an Austenite state, where it applies force on helical elastic element 404, thereby deforming it into a shape which is generally the same shape of the helical SMA element 402 (i.e., a wide circumference).

At a later time, the catheter tip 400 performs a transition from the wide circumference shape, back to the narrow circumference shape, by cooling the helical SMA element 402 below predetermined temperature $T_1$.

Accordingly, the helical SMA element 402 transforms into a Martensite state, where it becomes less rigid. Being in the Martensite state, the helical SMA element 402 is no longer able to apply sufficient force onto helical elastic element 404. Hence, the helical elastic element 404, retracting to its initial shape, deforms the helical SMA element 402, into a shape which is generally the same initial shape of the helical elastic element 404 (i.e., a narrow circumference).

According to a further aspect of the invention, which is illustrated in FIG. 9, the temperature-controlled fluid is provided through the guiding catheter 410 and released in the vicinity of the shape memory catheter tip. It is noted that the shape memory catheter tip can be cooled or heated, by this temperature-controlled fluid, to temperatures other than the temperature of the environment in which the tip is placed. When the supply of temperature controlled fluid stops, then the shape memory catheter tip is either cooled or heated to this environment temperature.

Figure 11:
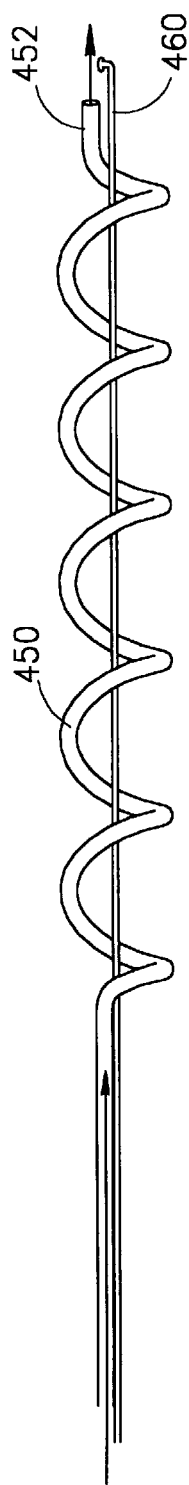
FIG. 11 is a schematic illustration of a catheter tip, constructed and operative in accordance with a further preferred embodiment of the present invention.

Reference is now made to FIG. 11, which is a schematic illustration of a catheter tip, generally referenced 450, constructed and operative in accordance with a further preferred embodiment of the present invention. Tip 450 is made of a hollow SMA tube, which enables the flow of temperature controlled fluid there through. The tip 450 is inserted in the body of the patient over a guiding wire 460.

According to this aspect of the invention, one end tip 450 is opened. The temperature controlled fluid, which is provided to the tip, travels through the tip 450 and is released through the tip end 452, in the vicinity of the shape memory catheter tip 450.

Figure 12:
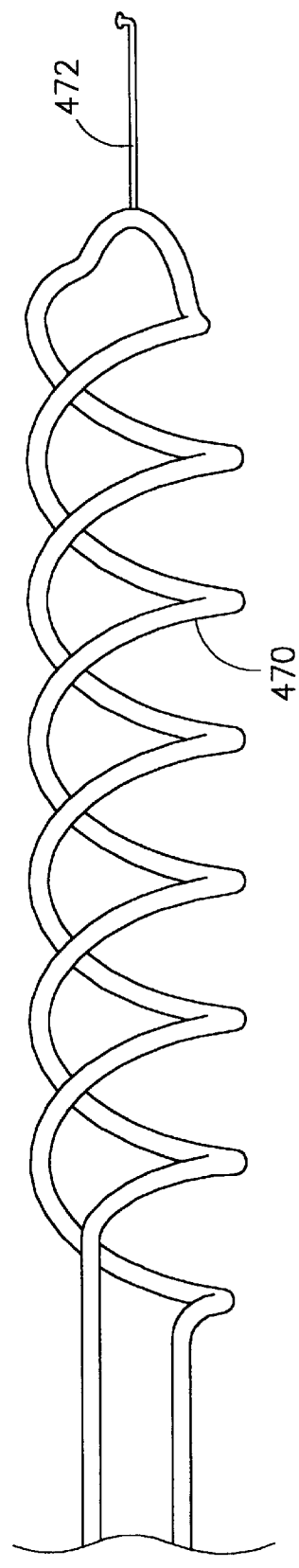
FIG. 12 is a schematic illustration of a catheter tip, constructed and operative in accordance with another preferred embodiment of the present invention.

Reference is now made to FIG. 12, which is a schematic illustration of a catheter tip, generally referenced 470, constructed and operative in accordance with another preferred embodiment of the present invention. Shape memory catheter tip 470 includes a guiding tip 472, which extends at the front of the tip 470. The shape memory catheter tip 470 is guided in the tubular organ to its destination, using this guiding tip, without the requirement of a guiding wire. It is noted that a guiding wire can also be used as further guiding assistance.

It is noted that each part of a catheter, according to the invention, and especially the catheter tip, can be coated with an anti-coagulation material such as Heparin.

Figure 13:
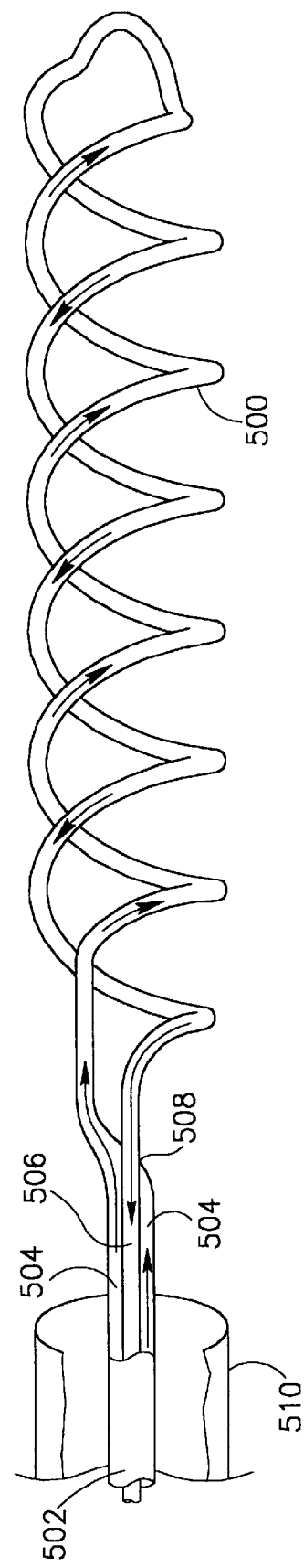
FIG. 13 is a schematic illustration of a catheter tip, and energy transfer means, constructed and operative in accordance with a further preferred embodiment of the present invention.

Reference is now made to FIG. 13, which is a schematic illustration of a catheter tip, generally referenced 500, and energy transfer means, generally referenced 502, constructed and operative in accordance with a further preferred embodiment of the present invention.

Energy transfer means include two concentric conduits 504 and 506, where conduit 504 is the outer conduit and conduit 506 is the inner conduit. The outer conduit 504 transfers the temperature-controlled fluid to the tip 500 and the inner conduit 506 receives temperature-controlled fluid from the tip and transfers it outside. It is noted that the directions of flow within the two conduits 504 and 506 can be swapped so that the inner conduit 506 transfers the temperature controlled fluid to the tip 500, while the outer conduit 504 transfers the temperature controlled fluid from the tip 500.

The entire assembly is generally inserted via a guiding catheter 510. It is noted that the concentric structure of the conduits provides reduced surface area and volume, so that a narrower guiding catheter can be used. Furthermore, the concentric structure provides a smoother shape, so that the movement of the conduits within the guiding catheter is easier.

According to another aspect of the present invention, a catheter is provided, which includes an integral SMA tip and a balloon mechanism. According to this aspect of the invention, the balloon is used to enlarge the diameter of the tip, while the SMA characteristics of the tip is used to reduce its diameter to its original size.

Figure 14A:
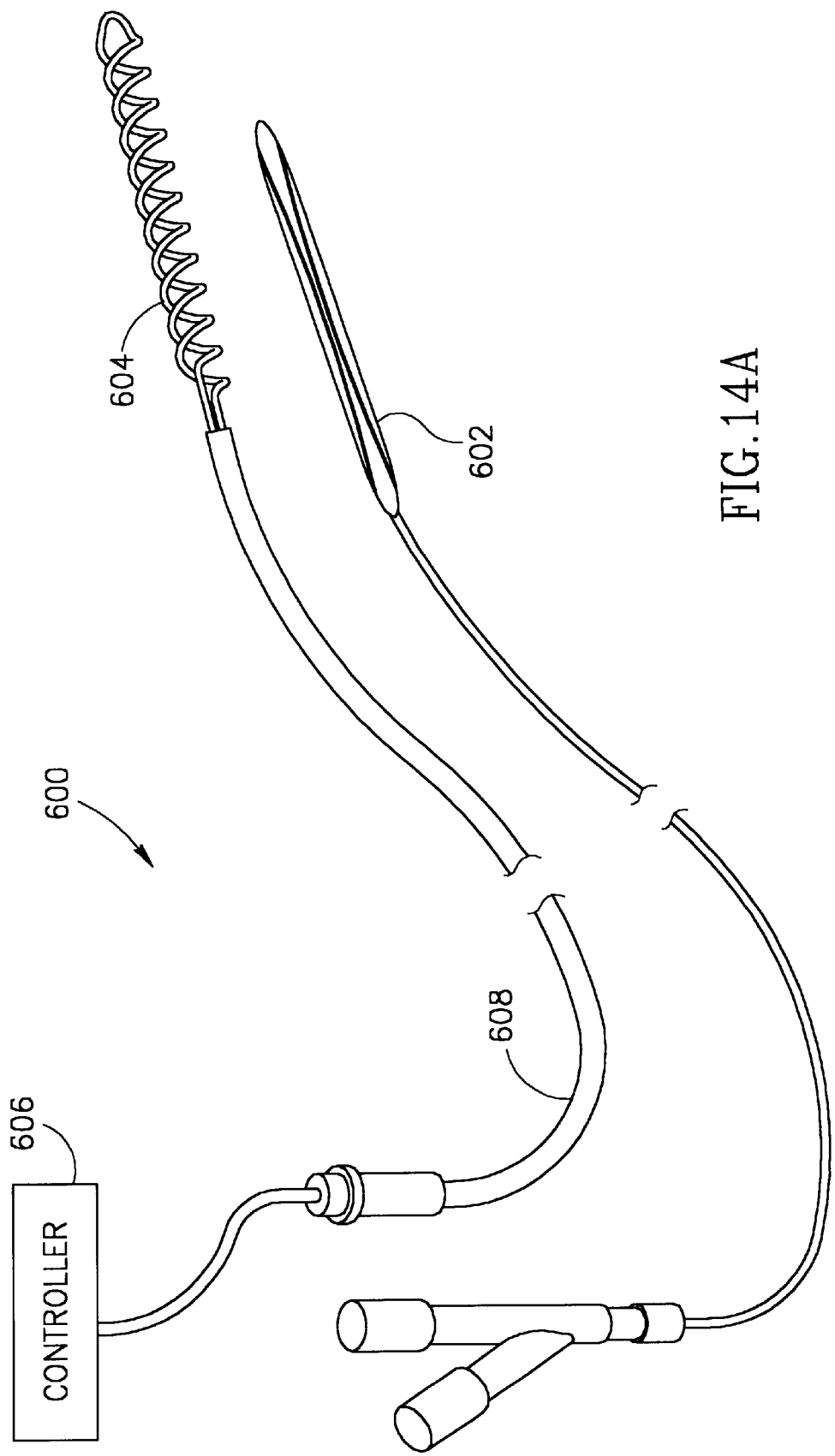
FIG. 14A is an illustration of a catheter system, constructed and operative in accordance with a further preferred embodiment of the present invention.

Reference is now made to FIG. 14A, which is an illustration of a catheter system, generally referenced 600, constructed and operative in accordance with a further preferred embodiment of the present invention.

System 600 includes a main catheter 608, an integrally connected catheter tip 604, a balloon mechanism 602 and a controller 606.

The tip 604 is a coil shaped element, made of a hollow tube, having a shape which is generally similar to the shape of tip 104, described hereinabove in conjunction with FIGS. 4A and 4B. It is noted that tip 604 has a large diameter shape when in the Martensite state and narrow diameter shape when in the Austenite state. It is noted the shape of the tip 604 can assume an initial shape having a narrow diameter, when in a Martensite.

Reference is further made to FIGS. 14B, 14C, 14D, 14E and 14F, which are illustrations of parts of system 600, inserted in an artery, generally referenced 610.

Figure 14B:
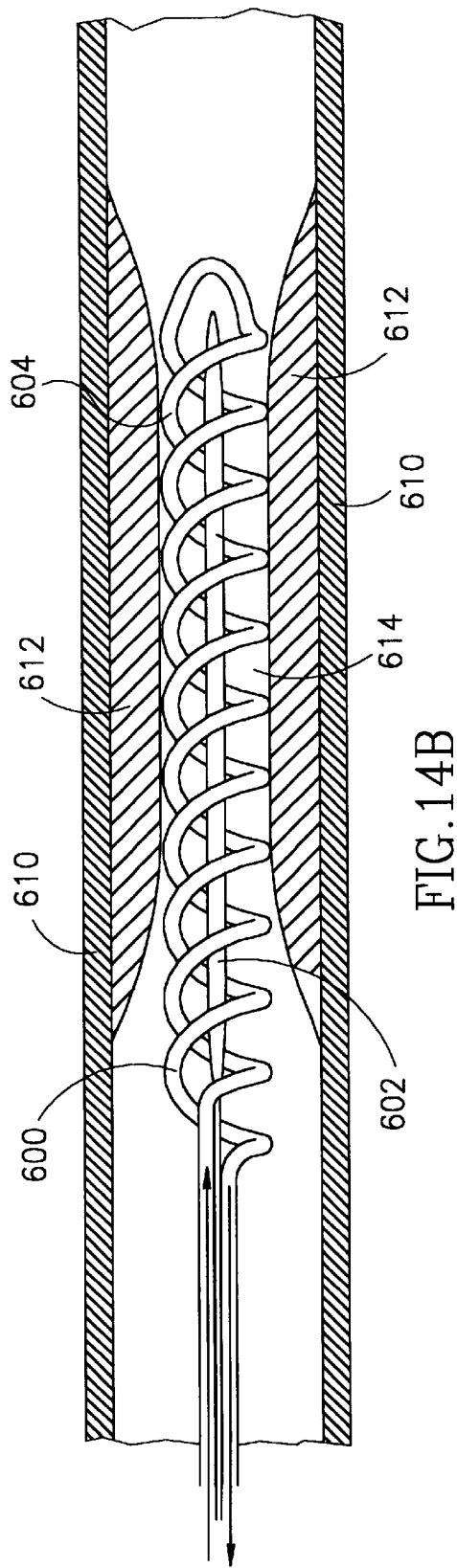
Figure 14C:
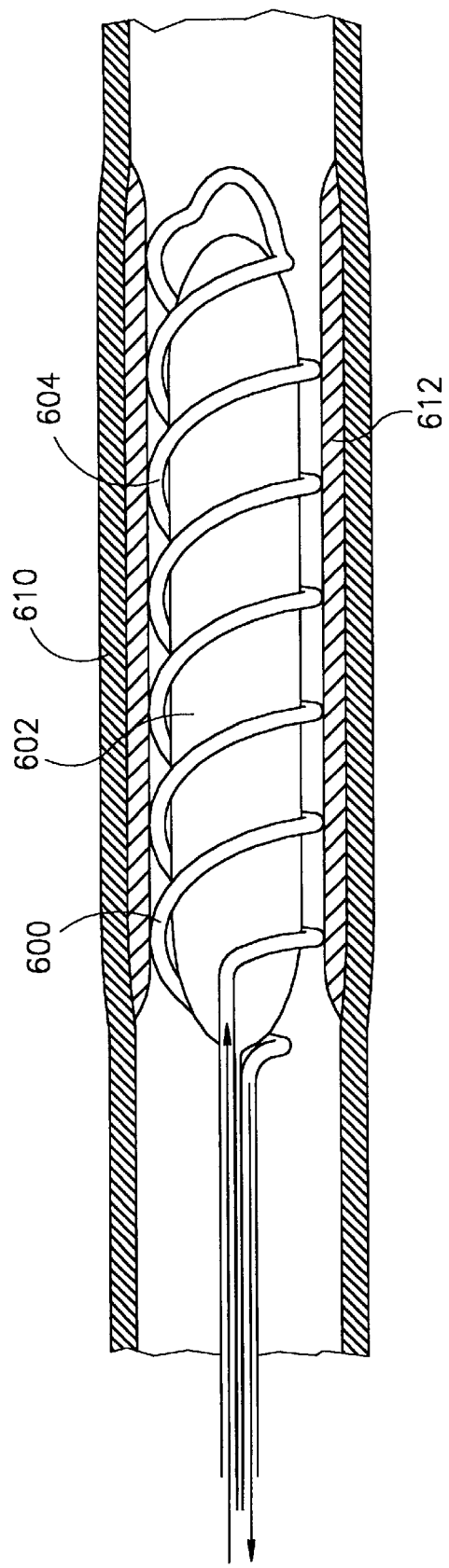

With reference to FIGS. 14B and 14C, the balloon 602 is inserted in the tip 604, so that the helical shape of the tip surrounds the balloon. The tip 604 and balloon 602 are inserted into an area, generally referenced 614, to be treated within artery 610 (FIG. 14B). As can be seen, the area, which is to be treated, is stenosed, thereby reducing the blood flow there through.

At this stage, tip 604 has a shape having a narrow diameter. Hence, the tip 604 is easily inserted in the artery 610. The physician locates the tip 604 in the artery 610 at the desired location, which, as can be seen from the drawing, suffers a major blockage 612, which significantly reduces flow there thorough.

Then, the physician operates the balloon mechanism and inflates the balloon 602. As the balloon 602 expands, it applies pressure on the tip 604, thereby enlarging its diameter (FIG. 14C). The inflation of the balloon 602 also pushes artery 610 walls and the blockage 612, outwardly, so as to increase the inner diameter thereof.

When the Balloon enlarges the artery 610 and tip 604 to the desired size, the physician operates the balloon mecha-nism so as to deflate the balloon (FIG. 14D). According to the present invention, the balloon deflates, thereby reducing the diameter of its shape, while the SMA tip maintains its large diameter shape, thereby supporting the walls of the treated section of the artery 610.

It is noted that term artery is presented only by way of example and that the present invention is applicable for any type of tubular organ.

As the balloon deflates, blood resumes its flow within the treated section of the artery, in both radial and axial directions. It is noted that since the tip 604 supports the walls of the treated section of the artery 610, then the physician can start deflating the balloon right after it reached the desired diameter. Accordingly, the time period in which the balloon blocks the treated section, thereby preventing blood flow, is significantly minimized to the order of few seconds. It is noted that at this stage, the balloon 602 can be removed from the treated section and for that matter, from the body of the patient. According to the present invention, the tip can remain in the artery, supporting the artery walls, for as long as required, to stabilize the shape of the artery in its new condition (FIG. 14D). The time period in which the tip supports the artery can be in the order of second, minutes, hours and even days.

When the artery is fixed in its new shape, then the physician operates system 600 so as to heat up the tip 604, thereby changing it into the Austenite state. Accordingly, the tip changes its shape by reducing its overall diameter (FIG. 14E). It is noted that the heating up of the tip can be performed in a plurality of ways such as pumping hot fluid through the tip 604. The arrows within the tip 604 (FIG. 14E) denote the flow of such fluid.

According to another aspect of the invention, the tip is heated by applying fluid to the vicinity of the tip, as shown in conjunction with FIG. 9.

According to a further aspect of the invention, when the transition temperature is located below body temperature, then the heating of the tip can be performed by use of the body temperature.

According to yet another aspect of the invention, when the transition temperature is located above body temperature, then the cooling of the tip can be performed by use of the body temperature.

According to yet a further aspect of the invention, the tip is heated by applying electric current therethrough, for example, as shown in conjunction with FIG. 8 and as will be described in detail herein below, in conjunction with FIG. 15.

Figure 14F:
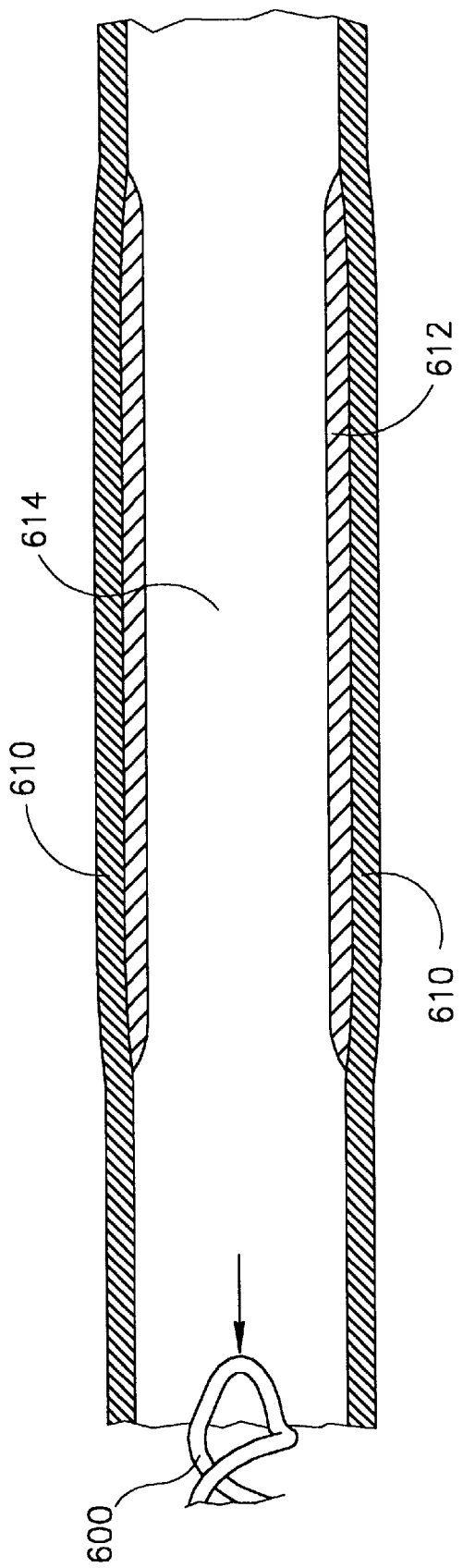

As the tip 604 shrinks, it is no longer attached to the walls of the artery and the physician can easily remove it from the treated section of the artery (FIG. 14F).

At this stage, the physician can remove the catheter from the body of the patient. However, it is noted that the physician can also move the catheter tip 604 to a new location within the artery system, which can be treated sequentially. Hence, the present invention incorporates an advantage over the prior art, where the catheter tip 604 can be used for more than one treatment.

It is noted that for an additional treatment, a new balloon can be provided and inserted to the tip 604. Alternatively, if the balloon 602 structure permits it, then the balloon 602 can be reused in the other location.

According to the present invention, when catheter tip is reused in a new location, it is first cooled down so as to move to a Martensite state, where it can be deformed by an inflating balloon. Such a cool down procedure can be performed by pumping cold fluid therethrough or by applying cold fluid to the vicinity of the tip.

Figure 15:
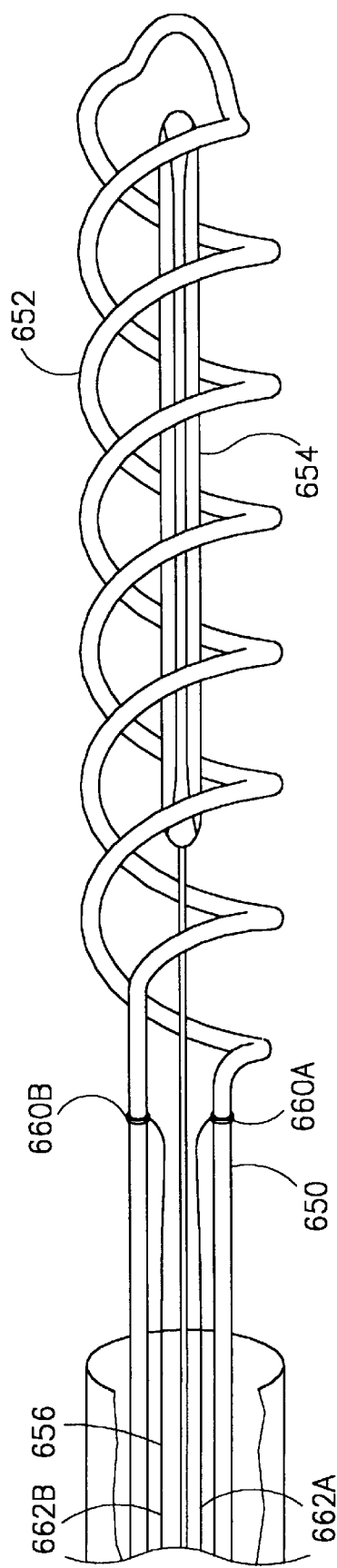
FIG. 15 is an illustration of a combined catheter tip and balloon assembly, constructed and operative in accordance with another preferred embodiment of the present invention.

Reference is now made to FIG. 15, which is an illustration of a combined catheter tip and balloon assembly, generally referenced 650, constructed and operative in accordance with another preferred embodiment of the present invention.

Assembly 650 includes a catheter tip 652, a balloon 654 and electrical heating means 656. The catheter tip 652 is made of solid SMA material, and has the shape of a general helix. The electrical heating means include two electrical wires 662A and 662B and two contact rings 660A and 660B.

The Balloon 654 is inserted within the tip 652. Contact rings 660A and 660B are each connected to the tip 652 at a different location, which defines an electrical path therebetween. The wires 662A and 662B are connected to contact rings 660a and 660B, respectively.

When the balloon 654 is inflated, it pushes the tip structure outwardly, thereby enlarging the diameter of the helix. It is noted that at this stage the tip is maintained in a Martensite state.

The wires 662A and 662B apply electrical current onto the tip 652, thereby heating it. When the tip 652 heats-up, it moves from the Martensite state to the Austenite state, thereby reducing the diameter of the helix.

According to another aspect of the present invention a catheter is provided, which includes a variety of integrally connected SMA catheter tips. These catheter tips have general cylindrical shapes or near cylindrical shapes, as will be described herein below.

Reference is now made to FIGS. 16A and 16B, which are illustrations of a catheter system, generally referenced 700, constructed and operative in accordance with a further preferred embodiment of the present invention.

System 700 includes a dilation catheter 712, a mounting catheter 716 integrally connected to a catheter tip 710, a guiding wire 718 and a controller 714. The controller 714 is generally connected to the tip section, via the dilation catheter and is operative to affect the temperature in which the catheter tip operates, either by controlling the temperature of the catheter tip itself or by controlling the temperature in the vicinity of the catheter tip. Mounting catheter 716 is used to maneuver the catheter tip 710 to its appropriate location, within the tubular organ, which for example is an artery. The guiding wire 718 is inserted through the mounting catheter 716 and the catheter tip 710.

The catheter tip 710 is made of shape memory alloy and is designed to have a first shape, when in the Martensite state and a second shape when in the Austenite state.

It is noted that the shape of the tip can be selected from a variety of shapes, which are generally cylindrical, as will be described herein below.

According to one aspect of the invention, the first shape has an overall diameter, which is generally narrower than the diameter of the second shape. Hence, changing the tip 710 from Martensite state to Austenite state, enlarges the overall diameter.

According to another aspect of the invention, the first shape has an overall diameter, which is generally wider than the diameter of the second shape. Hence, changing the tip 710 from Martensite state to Austenite state, reduces the overall diameter.

Tip 710 is made of a perforated structure or a plurality of wires, which are arranged in a mesh like structure (FIG. 16B).

Figure 17A:
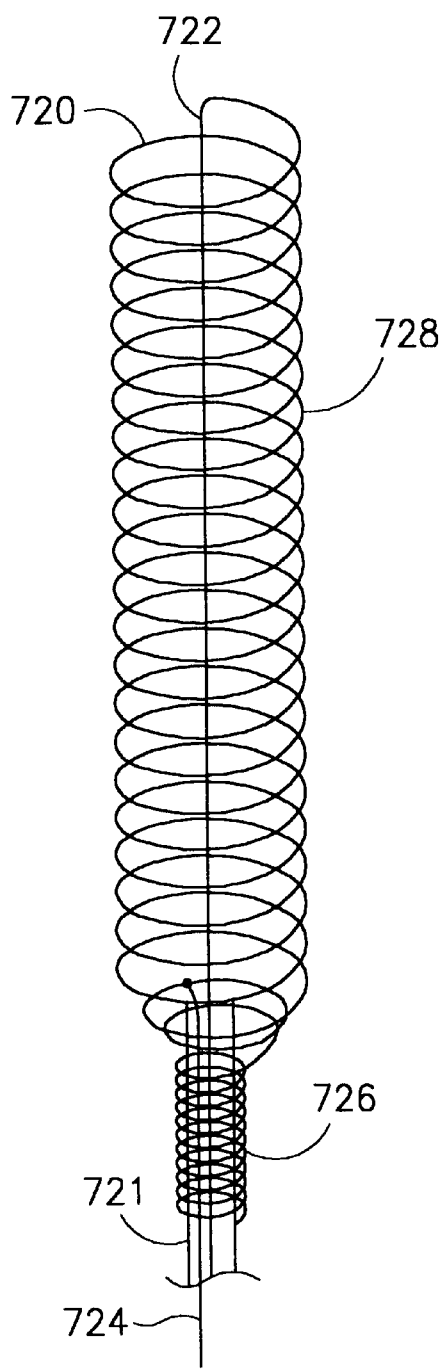
FIGS. 17A and 17B are illustrations of helical catheter tip, constructed and operative in accordance with another preferred embodiment of the invention.
Figure 17B:
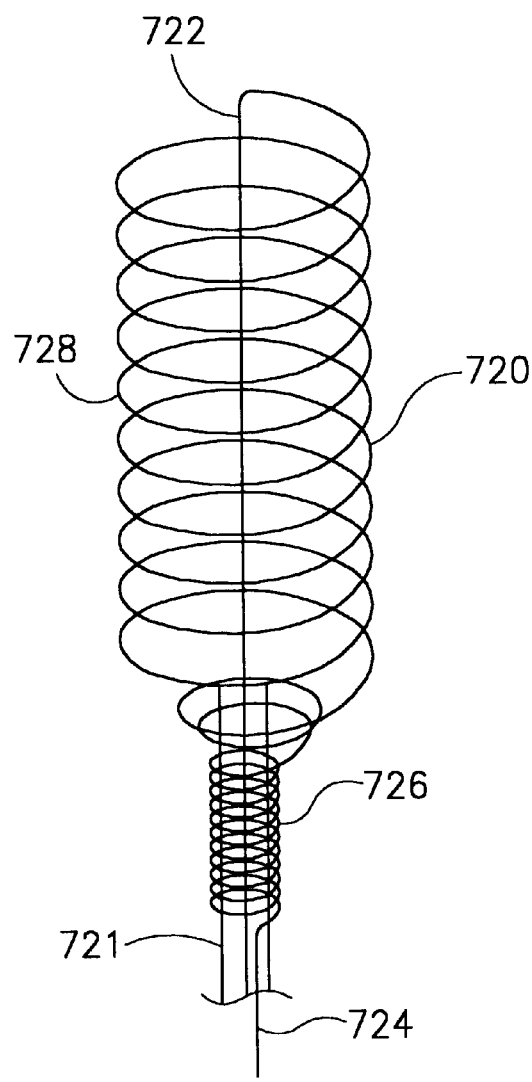

Reference is now made to FIGS. 17A and 17B, which are illustrations of helical catheter tip, generally referenced 720, constructed and operative in accordance with another preferred embodiment of the invention.

Tip 720 includes a dynamic section 728 and a tie-down section 726. Dynamic section 728 is made of shape memory alloy and is operative to expand and reduce its diameter. The tie-down section 726 is made of any type of alloy, and is firmly attached to the mounting catheter 721. It is noted that mounting catheter 721 is generally similar to mounting catheter 716, shown in conjunction with FIGS. 16A and 16B.

It is noted that since the tie-down section is firmly connected to the mounting catheter 721, then there is no significance to the type of alloy it is made of, since no shape deformation is allowed.

Tip 720 is electrically connected to a controlled power supply (not shown) using two electrical wires 722 and 724, each connected to another end of the SMA section 728. Hence, the tip 720 can be heated by means of electrical current, which is provided by the controlled power supply (not shown) and conducted by wires 722 and 724.

Tip 720 can be cooled by temperature controlled fluid, which is released in the vicinity of the tip 720 (conveyed by a dilation catheter such as dilation catheter 712 of FIG. 16A). Similarly, tip 720 can also be heated by such a temperature-controlled fluid, when provided at the appropriate temperature.

Reference is now made to FIGS. 18A, 18B, 18C and 18D, which are illustrations of an alternative catheter tip, generally referenced 730, constructed and operative in accordance with another preferred embodiment of the invention. FIG. 18A provides a view from the side of the tip in its reduced diameter shape, while FIG. 18B provides a view from the side of the tip in its expanded diameter shape. FIGS. 18C and 18D provide a view from the bottom of the respective views of FIGS. 18A and 18B.

Catheter tip 730 is integrally connected to a mounting catheter 732, which is used to maneuver the catheter tip to its appropriate location, within the tubular organ, which for example, is an artery.

Catheter tip 730 has a shape of a folded foil (FIGS. 18A and 18C), which expands (FIGS. 18B and 18D) during a phase transition. The tip 730 is attached to the mounting catheter 732 by a plurality of flexible elements (FIG. 18C) which are stretched during shape expansion (FIG. 18D).

Reference is further made to FIG. 18E, which is an illustration of an alternative foil shaped catheter tip, generally referenced 736, constructed and operative in accordance with a further aspect of the invention. The foil from which tip 736 made is fitted with a plurality of holes, generally referenced 734, which enable radial flow therethrough.

Figure 19A:
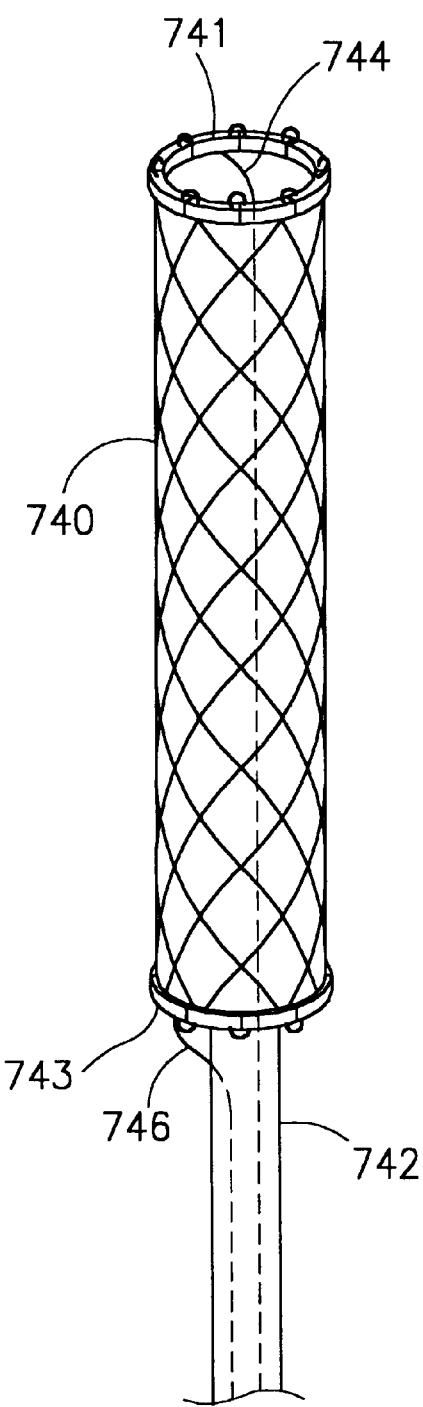
FIGS. 19A and 19B are illustrations of a catheter tip, constructed and operative in accordance with a further aspect of the invention.
Figure 19B:
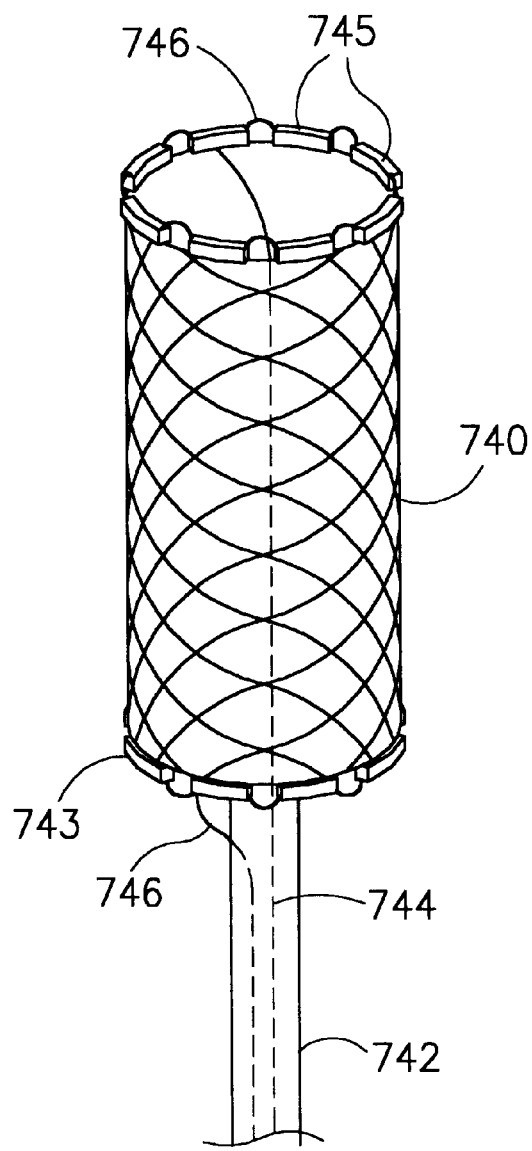

Reference is further made to FIGS. 19A and 19B, which are illustrations of a catheter tip, generally referenced 740, constructed and operative in accordance with a further aspect of the invention. Tip 740 is firmly attached to a mounting catheter 742. Tip 740 is a mesh like cylinder shaped tip, made of shape memory alloy. Tip 740 assumes a narrow diameter shape when changing to a first phase. Tip 740 assumes a wide diameter shape, when changing to a second phase. It is noted that the initial shape of the tip 740 is preferably one having a narrow diameter.

According to one aspect of the invention, the first phase is Martensite and the second phase is Austenite and hence, heating the tip 740 from the Martensite temperature to an Austenite temperature, will make it wider. According to another aspect of the invention, the first phase is Austenite and the second phase is Martensite and hence, heating the tip 740 from the Martensite temperature to an Austenite temperature, will make it narrower.

Catheter tip 740 further includes two conductive rings, 741 and 743, which are made of conductive material. Ring 743 is attached to the lower end of catheter tip 740. Ring 741 is attached to the higher end of catheter tip 740. Rings 741 and 743 are used to evenly spread an electrical current through tip 740. Each of the rings is made of a plurality of arcs 745, which are electrically connected by electrical bridges 746. This structure provides flexibility and high conductivity.

A first wire 746 is connected to ring 743 and a second wire 744 is connected to ring 741. Wires 744 and 746 are used to conduct electrical current to and from the tip 740, via conductive rings 741 and 743.

Figure 20:
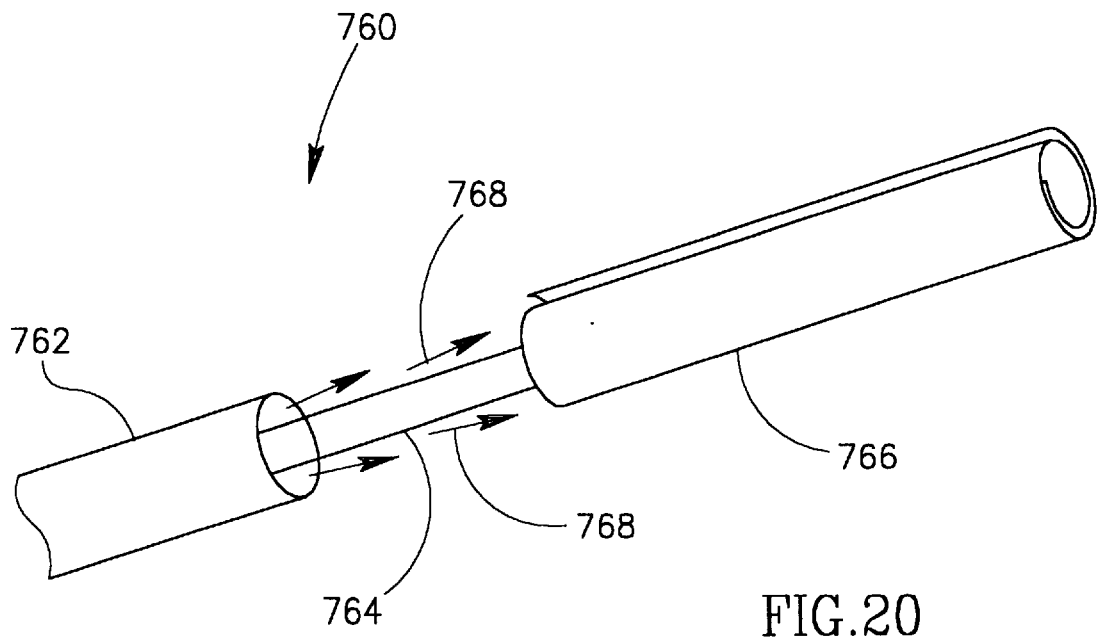
FIG. 20 is a schematic illustration of the tip area of a catheter system, constructed and operative in accordance with another preferred embodiment of the present invention.

Reference is now made to FIG. 20, which is a schematic illustration of the tip area of a catheter system, generally referenced 760, constructed and operative in accordance with another preferred embodiment of the present invention. FIG. 20 shows one way, according to the present invention, for controlling the temperature in the vicinity of the tip.

System 760 includes a dilation catheter 762, a mounting catheter 764, and a catheter tip 766, integrally connected thereto. The mounting catheter 764 is inserted through the dilation catheter 762. As can be seen from the drawing, temperature controlled fluid, generally designated 768, is released in the vicinity of the catheter tip 766. It is noted that this method is applicable to all of the catheter tips, which are disclosed herewith. It is further noted that by controlling the temperature of the fluid, the catheter tip can either be heated or cooled.

Figure 21:
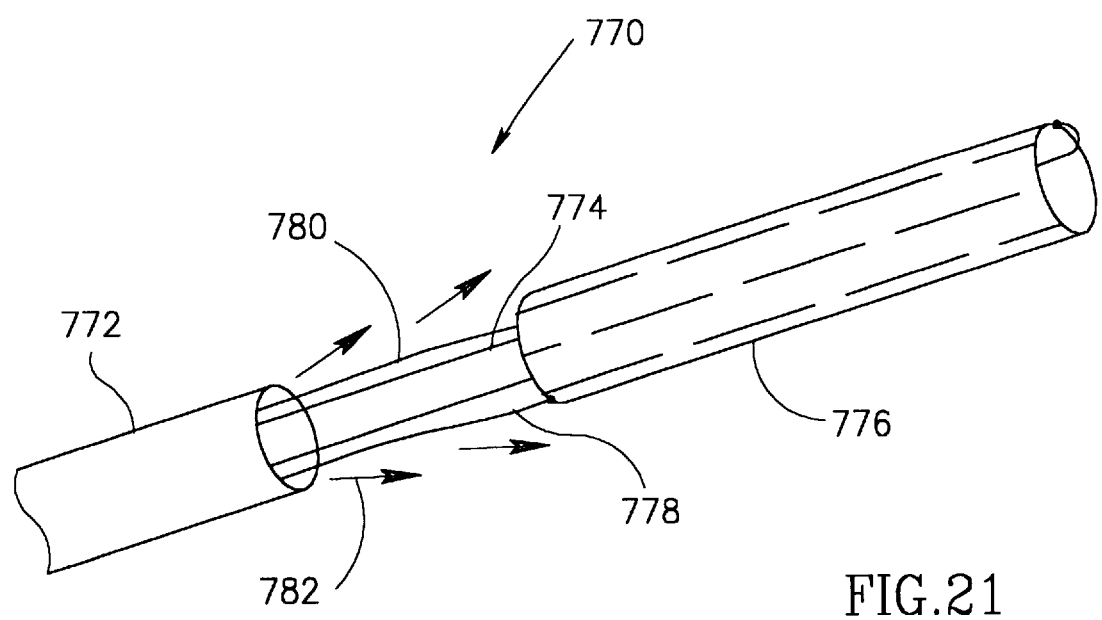
FIG. 21 is a schematic illustration of the tip area of a catheter system, constructed and operative in accordance with another preferred embodiment of the present invention.

Reference is now made to FIG. 21, which is a schematic illustration of the tip area of a catheter system, generally referenced 770, constructed and operative in accordance with another preferred embodiment of the present invention. FIG. 21 shows another way, according to the present invention, for controlling the temperature in the vicinity of the tip, where the tip is heated electrically and cooled by means of temperature controlled fluid.

System 770 includes a dilation catheter 772, a mounting catheter 774, and a catheter tip 776, integrally connected thereto. The mounting catheter 774 is inserted through the dilation catheter 772. The catheter tip 776 is electrically connected to an external power source (not shown) by means of electrical wires 778 and 780, each connected to another end of the catheter tip 776.

The catheter tip 776 is heated up when electrical current provided by the power supply, flows therethrough. The catheter tip 776 is cooled by means of temperature controlled fluid, generally designated 782, which is released in the vicinity of the catheter tip 776.

Reference is now made to FIGS. 22A and 22B. FIG. 22A is a schematic illustration of a catheter system, generally referenced 800, constructed and operative in accordance with another preferred embodiment of the present invention. FIG. 22B is an illustration in detail of a portion of the system 800 of FIG. 22A.

System 800 includes a dilation catheter 814, a mounting catheter 812, an SMA catheter tip 810, a controller 802 and a balloon mechanism 822. The balloon mechanism includes a directing mechanism 824, and a balloon tip 820. The catheter tip 810 is integrally connected to the mounting catheter 812, which is further connected to the controller 802.

When the catheter tip is changed from a Martensite state to an Austenite state, it assumes a shape having a narrow (reduced) diameter. The catheter tip 810 can be manufactured in a plurality of methods, so as to have a narrow diameter shape both in the Martensite state and in the Austenite state.

According to the present invention, the catheter tip is inserted to the body of the patient having the reduced diameter shape and being in a Martensite state, which provides enhanced flexibility. This flexibility is necessary for enabling the balloon to overcome the structural force of the catheter tip, thereby enlarging its diameter.

At first, the physician inserts the dilation catheter 814 into the body of the patient, through the artery system (not shown), and directs it to the vicinity of the stenosed section (not shown) which needs to be treated. Right after, the physician inserts the catheter tip 810 with the balloon 820 and mounting catheter 812 through the dilation catheter 814 and places the catheter tip 810 in the artery, at the artery section which is to be treated.

Then, the physician operates the balloon mechanism, so as to inflate the balloon 820. As the balloon 820 inflates it applies radial force on the walls of the catheter tip 810, thereby expanding its diameter (FIG. 22B). Immediately after the catheter tip 810 stabilizes within the artery walls and supports them in their expanded position, the physician deflates the balloon and can remove it from the location of the catheter tip. It is noted that the SMA catheter tip 810 is maintained in a temperature, which is typical to a Martensite phase.

After a predetermined period of time, which can be in the order of seconds, minutes, hours and even days, the catheter tip is heated to a temperature, which is typical to an Austenite phase and immediately deforms its shape so as to assume the narrow diameter shape. The narrow diameter shape is narrower than the new diameter of the treated artery section. At this stage, the catheter tip can be removed from the treated artery section.

According to the present invention, the SMA catheter tip is integrally connected to the dilation catheter. Hence, the dilation catheter remains within the body of the patient during the entire period of the treatment.

It is noted that system 800 can be fitted with any of the mounting catheter and catheter tip combination, which are presented hereinabove.

Figures 23A, 23B, 23C:
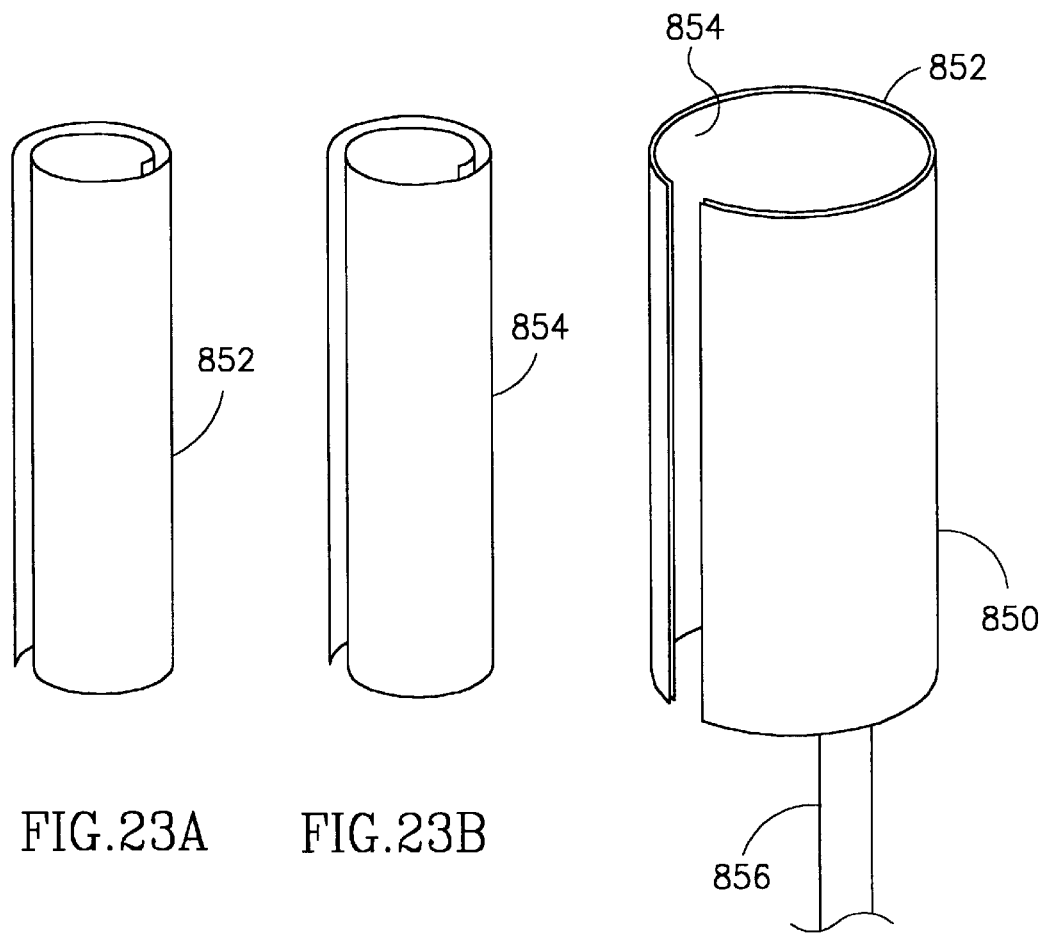
FIG. 23A is an illustration of an elastic spring layer, constructed and operative in accordance with a further preferred embodiment of the present invention.
FIG. 23B is an illustration of an SMA layer, in a Martensite state.
FIG. 23C is an illustration of a catheter tip, constructed and operative in accordance with another preferred embodiment of the present invention.
Figures 23D, 23E:
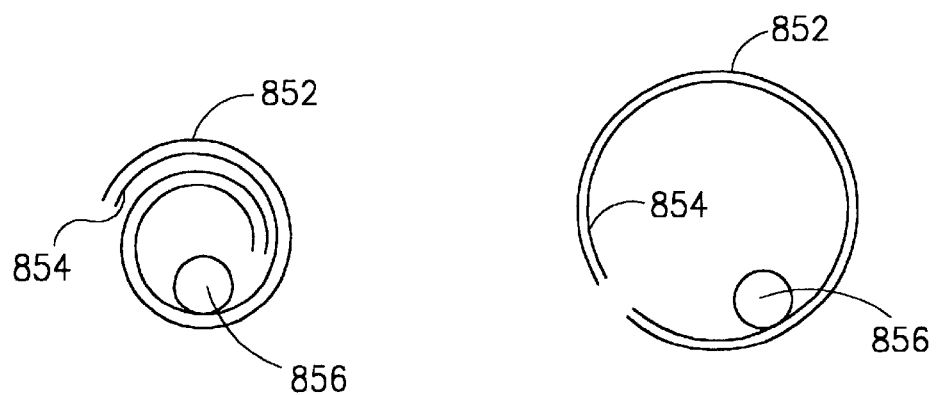
FIG. 23D is a view from the bottom of the catheter tip of FIG. 23C, in the narrowed state.
FIG. 23E is a view from the bottom of the catheter tip of FIG. 23C, in the widened state.

Reference is now made to FIGS. 23A, 23B, 23C, 23D and 23E. FIG. 23A is an illustration of an elastic spring layer, generally referenced 852, constructed and operative in accordance with a further preferred embodiment of the present invention. FIG. 23B is an illustration of an SMA layer, generally reference 854 in a Martensite state. FIG. 23C is an illustration of a catheter tip, generally referenced 850, constructed and operative in accordance with another preferred embodiment of the present invention. FIG. 23D is a view from the bottom of the catheter tip of FIG. 23C, in the narrowed state. FIG. 23E is a view from the bottom of the catheter tip of FIG. 23C, in the widened state.

Catheter tip 850 includes the SMA layer 854 and the elastic spring layer 852, attached thereto. The catheter tip 850 is integrally attached to a mounting catheter 856.

The diameter of elastic spring layer 852 is slightly narrower than the diameter of the SMA layer 854 when in the Martensite shape (FIG. 23B) so that the elastic spring layer 852 applies constant radial force onto the SMA layer 854, to reduce its diameter. When the SMA layer 854 is heated to the appropriate temperature, it moves from a Martensite phase to an Austenite phase and consequently deforms its shape to become a wider cylinder (FIGS. 23C and 23E). It is noted that the deformation force which is provided by the SMA layer 854, in the Austenite phase, is greater than the retraction force, which is provided by the elastic spring layer 852.

When the catheter tip 850 is cooled to a temperature, which is typical for a Martensite state, then the SMA layer 854 becomes weaker, more flexible and no longer provides an outwardly directed deformation force. At this stage, the retraction force, is the greater one and hence, the elastic spring layer 852 forces the SMA layer 854 to reduce its diameter and retract to a shape having a narrower diameter (FIGS. 23B and 23D).

It is noted that such an elastic spring layer can be fitted to any of the catheter tips, which are disclosed hereinabove. In other words, any one of the above SMA catheter tips can replace the SMA layer 854.

Figure 24A:
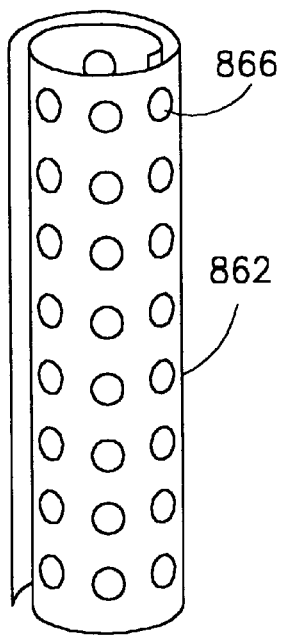
FIG. 24A is an illustration of an elastic spring layer, constructed and operative in accordance with a further preferred embodiment of the present invention.
Figure 24B:
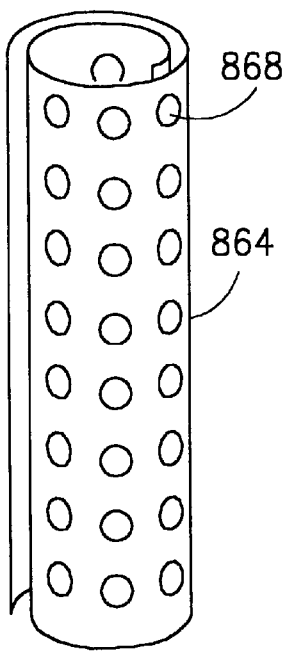
FIG. 24B is an illustration of an SMA layer in a Martensite state.
Figure 24C:
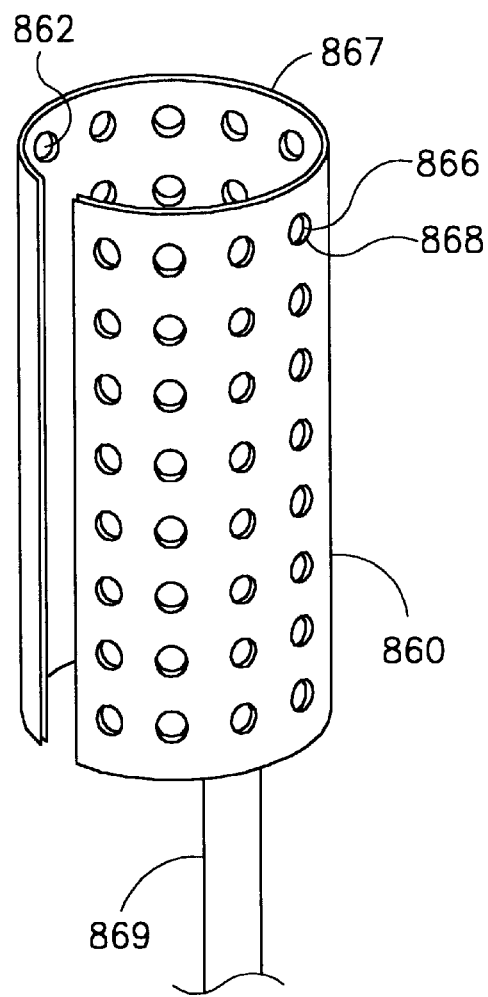
FIG. 24C is an illustration of a catheter tip, constructed and operative in accordance with another preferred embodiment of the present invention.

Reference is now made to FIGS. 24A, 24B and 24C. FIG. 24A is an illustration of an elastic spring layer, generally referenced 862, constructed and operative in accordance with a further preferred embodiment of the present invention. FIG. 24B is an illustration of an SMA layer, generally reference 864 in a Martensite state. FIG. 24C is an illustration of a catheter tip, generally referenced 860, constructed and operative in accordance with another preferred embodiment of the present invention.

SMA layer 864 has a plurality of holes, generally referenced 868. The catheter tip 860 is integrally attached to a mounting catheter 869. Elastic spring layer 862 has a plurality of holes, generally referenced 866. Catheter tip 860 is includes the SMA layer 864 and the elastic spring layer 862, attached thereto in a way that each of the holes 868 faces a respective hole 866. Catheter tip 860 provides both axial and radial flow of fluid therethrough.

Figures 25A, 25B:
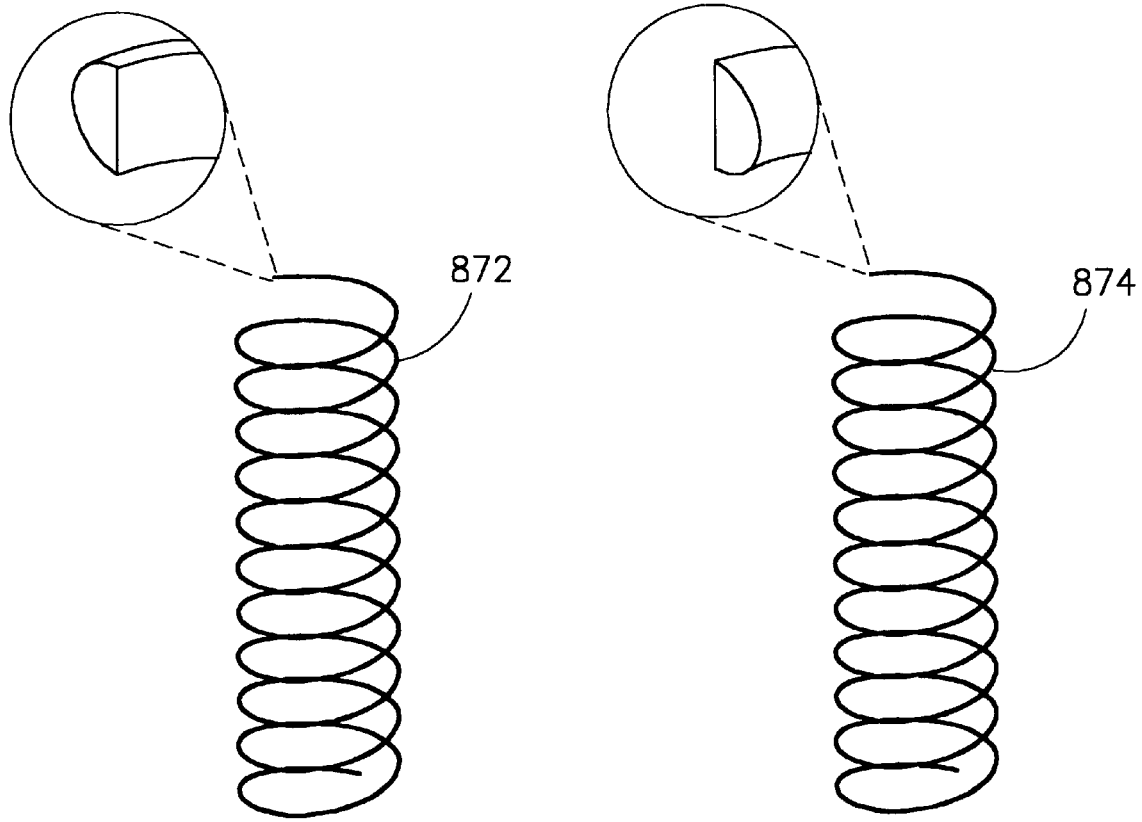
FIG. 25A is an illustration of an elastic spring helix, constructed and operative in accordance with a further preferred embodiment of the present invention.
FIG. 25B is an illustration of an SMA helix in a Martensite state.
Figure 25C:
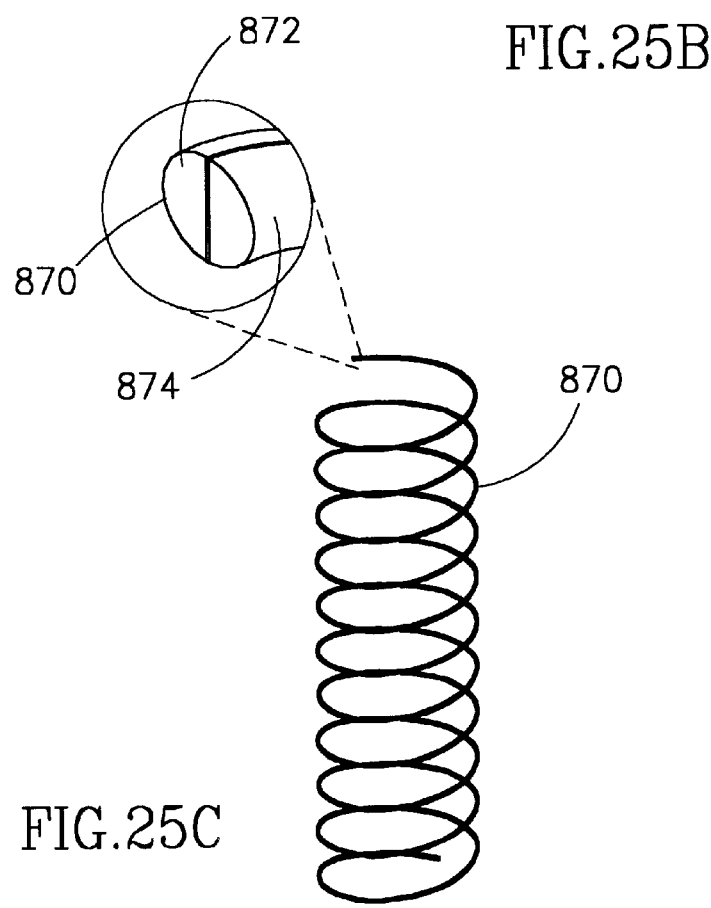
FIG. 25C is an illustration of a catheter tip, constructed and operative in accordance with another preferred embodiment of the present invention.

Reference is now made to FIGS. 25A, 25B and 25C. FIG. 25A is an illustration of an elastic spring helix, generally referenced 872, constructed and operative in accordance with a further preferred embodiment of the present invention. FIG. 25B is an illustration of an SMA helix, generally reference 874 in a Martensite state. FIG. 25C is an illustration of a catheter tip, generally referenced 870, constructed and operative in accordance with another preferred embodiment of the present invention.

Elastic spring helix 872 has a cross-section, which is shaped as an left-side half circle (see the enlarged section in FIG. 25A). SMA helix 874 has a cross-section, which shaped as an right-side half circle (see the enlarged section in FIG. 25B). Elastic spring helix 872 and SMA helix 874 are attached to each other to form catheter tip 870, where the cross-section of the catheter tip 870 is a complete circle (see the enlarged section in FIG. 25C). When the SMA helix 874 changes from Martensite to Austenite, it assumes a shape, which has a wider diameter than its initial diameter, thereby forcing elastic spring helix 872 to expand outwardly. When the SMA helix 874 changes from Austenite to Martensite, it becomes more flexible, thereby enabling the elastic spring helix 872 to overcome it and force it to return to the originally reduced diameter.

Figure 26C:
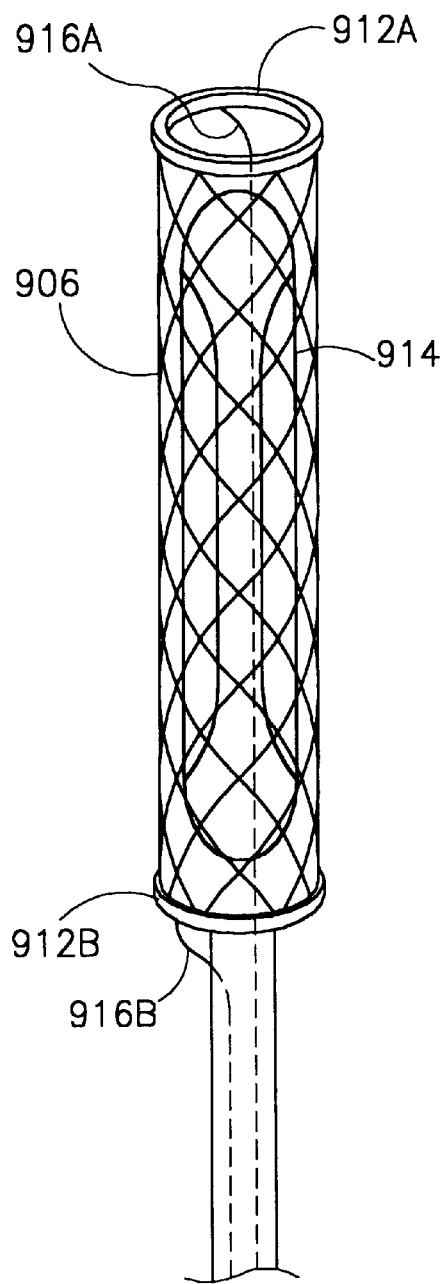
FIGS. 26C and 26D are enlarged illustrations of the catheter tip section of the system of FIG. 26A.
Figure 26D:
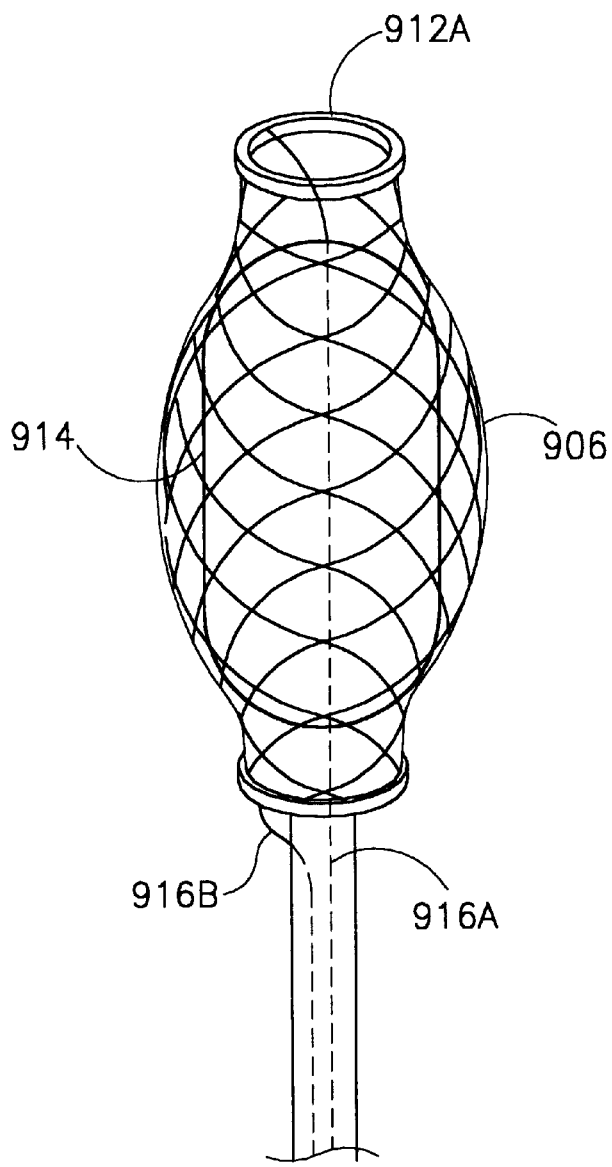

Reference is now made to FIGS. 26A, 26B, 26C and 26D. FIG. 26A is a schematic illustration of a catheter system, generally referenced 900, constructed and operative in accordance with another preferred embodiment of the present invention. FIG. 26B is an illustration in detail of a portion of the system 900 of FIG. 26A. FIGS. 26C and 26D are enlarged illustrations of the catheter tip section of system 900.

System 900 includes a dilation catheter 902, a mounting catheter 904, an SMA catheter tip 906, a controller 910 and a balloon mechanism 914 (FIGS. 26C and 26D) which is placed within the SMA catheter tip 906.

The SMA catheter tip 906 is a mesh-like catheter tip, which includes two electrically conductive rings 912A and 912B, each on either end. Ring 912A is attached to the upper end of the SMA catheter tip 906 and ring 912B is attached to the lower end of the SMA catheter tip 906. Rings 912A and 912B are connected to an electrical current source (not shown) via electrical wires 916A and 916B, respectively. The SMA catheter tip 906 is designed so that it shrinks when heated beyond a predetermined temperature, thereby reducing the overall diameter thereof.

The balloon 914 is shorter than the overall length of the SMA catheter tip 906 so that where it inflates, it widens the middle section of the SMA catheter tip 906, while the end sections remain at the original diameter.

According to this aspect of the invention, the balloon is fully retained within the catheter tip.

Figure 27A:
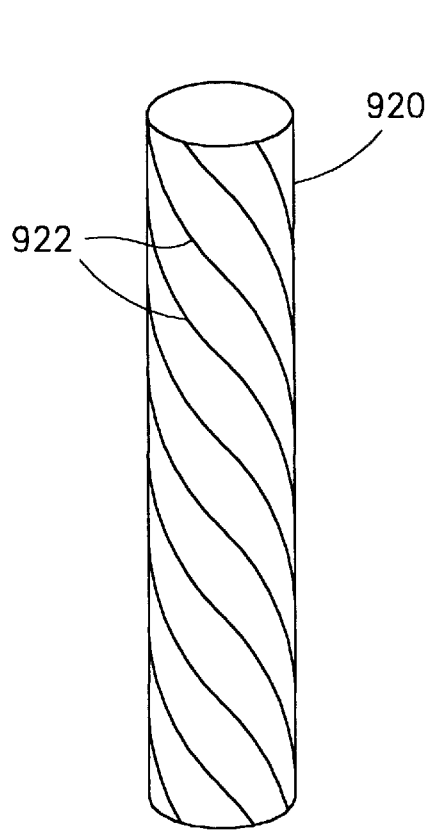
FIG. 27A is an illustration of an elastic structure, constructed and operative in accordance with a further preferred embodiment of the present invention.
Figure 27B:
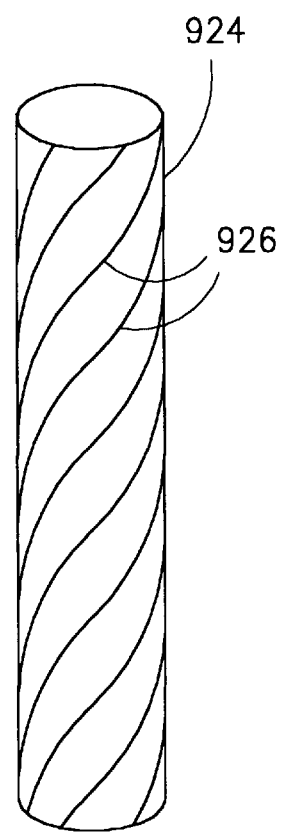
FIG. 27B is an illustration of an SMA structure, in a Martensite state.
Figure 27C:
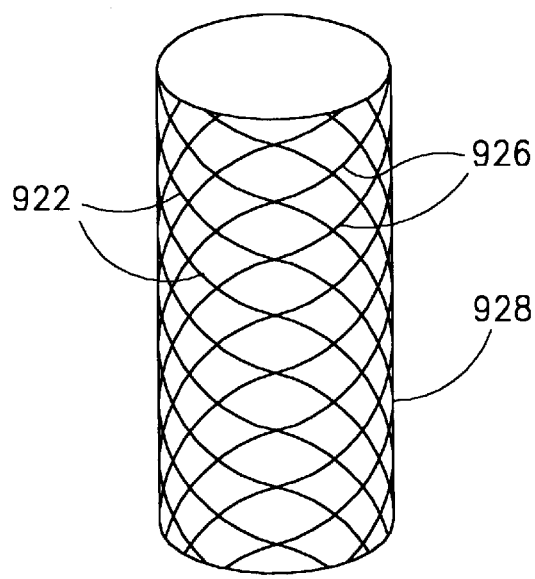
FIG. 27C is an illustration of a catheter tip, constructed and operative in accordance with another preferred embodiment of the present invention.

Reference is now made to FIGS. 27A, 27B and 27C. FIG. 27A is an illustration of an elastic structure, generally referenced 920, constructed and operative in accordance with a further preferred embodiment of the present invention. FIG. 27B is an illustration of an SMA structure, generally reference 924, in a Martensite state. FIG. 27C is an illustration of a catheter tip, generally referenced 928, constructed and operative in accordance with another preferred embodiment of the present invention.

Elastic structure 920 (FIG. 27A) is constructed as the length portion (references 922) of a crosswise structure. SMA structure 924 is constructed as the breadth portion (references 926) of a crosswise structure.

Elastic structure 920 and SMA structure 924 are attached (FIG. 27C), so as to form a crosswise structure. It is noted that the two parts can either be attached to each other, wherein one is the inner part and the other is the outer part of the crosswise structure. Alternatively, the two portions can be intertwined so as to form a web-like structure.

Catheter tip 928 operates in a manner, similar to the that of catheter tip 870 of FIG. 25C. Accordingly, when the SMA portion 924 is heated beyond a predetermined temperature, it moves into an Austenite state, where it expands thereby enlarging the diameter of the catheter tip 928. Afterwards, when the catheter tip 928 is cooled down, the SMA structure 924 moves to Martensite state and the elastic structure 920 forces the catheter tip 928 to reduce its diameter.

It will be appreciated by persons skilled in the art that the present invention is not limited to what has been particularly shown and described hereinabove. Rather the scope of the present invention is defined only by the claims which follow.

What is claimed is:

1. A system for opening and temporarily supporting a portion of a generally tubular organ, comprising, in combination:

a dilation catheter including a shape memory catheter tip which is both (a) integral with said catheter, and (b) incapable of being separated from said catheter during times when the system functions according to its intended purposes, said shape memory catheter tip including a portion thereof which is formed of a shape memory alloy, and said shape memory catheter tip being further formed with an internal lumen defined by a shape memory wall portion which is impermeable so as to prevent the escape of fluid from said internal lumen through said wall portion;

means for guiding said shape memory catheter tip to a selected location of an organ;

said shape memory catheter tip including means for enabling said tip to assume a first shape at a first temperature and means for causing said tip to assume a second shape at a second temperature, said first shape providing the functional temporary support of said tubular organ, said first temperature being lower than said second temperature, and wherein relative movement between said tip and said guiding means is possible during use.

2. The system according to claim 1, further comprising:

an energy control unit functionally connected to said shape memory catheter tip for controlling the temperature of said memory catheter tip, and energy transfer means functionally connected between said energy control unit and said shape memory catheter tip for transferring energy therebetween.

3. The system according to claim 2, wherein the energy transfer means comprises at least one conduit, and wherein said temperature control unit comprises means for providing temperature-controlled fluid towards said shape memory catheter tip via said energy transfer means.

4. The system according to claim 3, wherein said energy transfer means comprises two concentric conduits.

5. In a system for opening and temporarily supporting a section of a generally tubular organ, the system including a dilation catheter and an inflatable balloon, the dilation catheter including an integrally connected shape memory catheter tip, the shape memory catheter tip, being made of a shape memory alloy, the balloon being inserted within said shape memory catheter tip, a method for operating the system comprising the steps of:

inflating said balloon, thereby increasing the diameter of said shape memory catheter tip;

deflating said balloon, thereby enabling flow of bodily fluids through said shape memory catheter tip, heating said shape memory catheter tip to a predetermined temperature, thereby moving said shape memory catheter tip to an Austenite state which decreases the diameter of said shape memory catheter tip.

6. The method according to claim 5, further comprising the step of locating said shape memory catheter tip and said balloon in a selected area within a generally tubular organ.

7. The method according to claim 6, further comprising the step of inserting said shape memory catheter tip and said balloon into the body of the patient.

8. The method according to claim 5, further comprising the step of removing said shape memory catheter tip from said selected area.

\* \* \* \* \*